(12) United States Patent
Tan et al.

(10) Patent No.: US 12,084,631 B2
(45) Date of Patent: *Sep. 10, 2024

(54) MULTILAYER DISSOLVABLE SOLID ARTICLE AND METHOD OF MAKING SAME

(71) Applicant: The Procter & Gamble Company, Cincinnati, OH (US)

(72) Inventors: Hongsing Tan, Beijing (CN); Robert Wayne Glenn, Jr., Singapore (SG); Carl David MacNamara, Beijing (CN); Ming Tang, Beijing (CN); Toshiyuki Okada, Singapore (SG); Hongling Chen, Beijing (CN); Xu Huang, Beijing (CN); Gabrielle Alejandro Nogueira Meza, Cincinnati, OH (US); Min Jiang, Beijing (CN)

(73) Assignee: The Procter & Gamble Company, Cincinnati, OH (US)

(*) Notice: Subject to any disclaimer, the term of this patent is extended or adjusted under 35 U.S.C. 154(b) by 367 days.

This patent is subject to a terminal disclaimer.

(21) Appl. No.: 16/822,138

(22) Filed: Mar. 18, 2020

(65) Prior Publication Data

US 2020/0308517 A1    Oct. 1, 2020

(30) Foreign Application Priority Data

Mar. 25, 2019 (WO) ................ PCT/CN2019/079514

(51) Int. Cl.
*B29D 7/01* (2006.01)
*B32B 3/02* (2006.01)
(Continued)

(52) U.S. Cl.
CPC ............. *C11D 17/06* (2013.01); *C11D 1/146* (2013.01); *C11D 3/2065* (2013.01); *C11D 3/3753* (2013.01)

(58) Field of Classification Search
CPC .. A61K 8/0208; A61K 8/0233; A61K 8/8129; A61K 8/345; A61K 8/463;
(Continued)

(56) References Cited

U.S. PATENT DOCUMENTS 4,170,565 A   10/1979 Flesher et al.
4,557,852 A   12/1985 Schulz et al.
(Continued)

FOREIGN PATENT DOCUMENTS

| CA | 1242949 A | 10/1988 |
|----|-----------|---------|
| CH | 575453 A5 | 5/1976 |
| CN | 1202517   | 12/1998 |
| CN | 1202517 A | 12/1998 |
| CN | 2352536 Y | 12/1999 |
| CN | 1250085 A | 4/2000 |
| CN | 1421519 A | 6/2003 |
| CN | 1583991 A | 2/2005 |

(Continued)

OTHER PUBLICATIONS

PCT Search Report for appl. No. PCT/CN2019/079514, dated Dec. 25, 2019, 13 pages.
(Continued)

*Primary Examiner* — Brian P Mruk
(74) *Attorney, Agent, or Firm* — George H. Leal; Carrie Schwartz; Andres Ernesto Velarde

(57) ABSTRACT

This invention provides a multilayer dissolvable solid article, which comprises two or more flexible, dissolvable, porous sheets. Each of such two or more sheets is characterized by a Percent Open Cell Content of from about 80% to 100% and an Overall Average Pore Size of from about 100 μm to about 2000 μm and comprises a water-soluble polymer. At least two adjacent sheets in such dissolvable solid article are characterized by an Adhesion Score (AdS) of no less than 1, while the contacting surfaces of said at least two adjacent sheets are essentially free of adhesives. Preferably, (Continued)

the multilayer dissolvable solid article is essentially free of adhesives.

14 Claims, 7 Drawing Sheets

(51) Int. Cl.
    *B32B 5/32*           (2006.01)
    *B32B 7/10*           (2006.01)
    *C11D 1/00*           (2006.01)
    *C11D 1/14*           (2006.01)
    *C11D 3/20*           (2006.01)
    *C11D 3/37*           (2006.01)
    *C11D 17/06*          (2006.01)

(58) Field of Classification Search
    CPC .......... B29D 7/01; C11D 1/00; C11D 3/2041;
              C11D 3/2065; C11D 3/37; C11D 3/3753;
              C11D 17/042; C11D 17/06; B32B 3/02;
              B32B 3/266; B32B 5/32; B32B 7/10;
              B32B 2250/00; B32B 2250/24
    See application file for complete search history.

(56) References Cited

U.S. PATENT DOCUMENTS

| | | |
|---|---|---|
| 4,610,799 A | 9/1986 | Wilsberg et al. |
| 4,654,395 A | 3/1987 | Schulz et al. |
| 4,743,394 A | 5/1988 | Kaufmann et al. |
| 4,747,976 A | 5/1988 | Yang et al. |
| 4,806,261 A | 2/1989 | Ciallella et al. |
| 4,938,888 A | 7/1990 | Kiefer et al. |
| 5,202,045 A | 4/1993 | Karpusiewicz et al. |
| 5,479,798 A | 1/1996 | Mueller |
| 6,465,407 B2 | 10/2002 | Hayashi |
| 6,699,826 B1 | 3/2004 | Saijo |
| 6,818,606 B1 | 11/2004 | Hanada et al. |
| 7,094,744 B1 | 8/2006 | Kobayashi et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,367,596 B2 | 2/2013 | Fossum |
| 8,461,091 B2 | 6/2013 | Glenn, Jr. |
| 8,466,099 B2 | 6/2013 | Glenn, Jr. |
| 8,765,170 B2 | 7/2014 | Glenn, Jr. |
| 9,233,055 B2 | 1/2016 | Glenn, Jr. |
| 9,969,154 B2 | 5/2018 | Content |
| 11,376,312 B2 | 5/2022 | Jain |
| 11,525,104 B2 * | 12/2022 | Tan ...................... C11D 3/2065 |
| 11,713,179 B2 * | 8/2023 | Glenn, Jr. ............ C11D 17/044 |
| | | 222/1 |
| 2002/0091169 A1 | 7/2002 | Klotzer |
| 2005/0106233 A1 | 5/2005 | Andersen et al. |
| 2006/0009099 A1 | 1/2006 | Jonn et al. |
| 2006/0165760 A1 | 7/2006 | Pinna et al. |
| 2007/0218285 A1 | 9/2007 | Malessa |
| 2008/0020024 A1 | 1/2008 | Kulkarni et al. |
| 2009/0104420 A1 | 4/2009 | Nadella |
| 2009/0249558 A1 | 10/2009 | Fileccia |
| 2010/0291165 A1 | 11/2010 | Glenn, Jr. et al. |
| 2011/0027328 A1 | 2/2011 | Baig et al. |
| 2011/0132387 A1 | 6/2011 | Alwattari et al. |
| 2011/0136719 A1 | 6/2011 | Jalbert et al. |
| 2011/0195098 A1 | 8/2011 | Glenn, Jr. et al. |
| 2011/0200649 A1 | 8/2011 | Schwartz |
| 2012/0231691 A1 | 9/2012 | Peyras-carratte et al. |
| 2012/0270029 A1* | 10/2012 | Glenn, Jr. ................ A61Q 5/02 |
| | | 428/221 |
| 2014/0248400 A1 | 9/2014 | Phonchareon et al. |
| 2015/0159330 A1 | 6/2015 | Weisman et al. |
| 2015/0218497 A1 | 8/2015 | Jalbert et al. |
| 2016/0044935 A1 | 2/2016 | Aldred et al. |
| 2016/0296432 A1 | 10/2016 | Delmas et al. |
| 2017/0234618 A1 | 8/2017 | Guo |
| 2021/0236394 A1 | 8/2021 | Fan et al. |
| 2021/0236395 A1 | 8/2021 | Fan et al. |

FOREIGN PATENT DOCUMENTS

| | | | |
|---|---|---|---|
| CN | 101384425 A | 3/2009 | |
| CN | 102325517 A | 1/2012 | |
| CN | 102492573 A | 6/2012 | |
| CN | 102492573 U | 6/2012 | |
| CN | 102647974 A | 8/2012 | |
| CN | 102732392 A | 10/2012 | |
| CN | 102762612 A | 10/2012 | |
| CN | 202744521 | 2/2013 | |
| CN | 202744521 U | 2/2013 | |
| CN | 202754982 U | 2/2013 | |
| CN | 102965223 A | 3/2013 | |
| CN | 202754982 | 3/2013 | |
| CN | 103596624 A | 2/2014 | |
| CN | 103740490 A | 4/2014 | |
| CN | 104403644 A | 3/2015 | |
| CN | 104874801 A | 9/2015 | |
| CN | 105238584 A | 1/2016 | |
| CN | 105462733 A | 4/2016 | |
| CN | 105586165 A | 5/2016 | |
| CN | 105647716 A | 6/2016 | |
| CN | 205398584 U | 7/2016 | |
| CN | 105861168 A | 8/2016 | |
| CN | 105886142 A | 8/2016 | |
| CN | 205420320 | 8/2016 | |
| CN | 205420320 U | 8/2016 | |
| CN | 106635572 | 12/2016 | |
| CN | 106795353 A | 5/2017 | |
| CN | 105199887 A | 10/2018 | |
| EP | 0234867 A2 | 9/1987 | |
| EP | 234867 A3 | 9/1987 | |
| FR | 2996768 A1 | 4/2014 | |
| JP | S5871878 A | 4/1983 | |
| JP | S59230737 A | 12/1984 | |
| JP | 3008496 A | 1/1988 | |
| JP | 63012466 A | 1/1988 | |
| JP | S638496 A | 1/1988 | |
| JP | S6312466 A | 1/1988 | |
| JP | 63150396 A | 6/1988 | |
| JP | S63150396 A | 6/1988 | |
| JP | 04202600 A | 7/1992 | |
| JP | H04202600 A | 7/1992 | |
| JP | 2002201500 A | 7/2002 | |
| JP | 2006027024 A | 2/2006 | |
| JP | 2009190236 A | 8/2009 | |
| JP | 4509284 B2 | 7/2010 | |
| JP | 2017518392 A | 7/2017 | |
| KR | 20090036882 A | 4/2009 | |
| KR | 20090036883 A | 4/2009 | |
| KR | 20100090122 A | 8/2010 | |
| KR | 20100096985 A | 9/2010 | |
| KR | 101146292 B1 | 5/2012 | |
| KR | 20120127174 A | 11/2012 | |
| KR | 20120130693 A | 12/2012 | |
| KR | 20080111815 A | 1/2013 | |
| RU | 2323715 C1 | 5/2008 | |
| RU | 2625433 C1 | 7/2017 | |
| WO | 0108658 A1 | 2/2001 | |
| WO | 2009022909 A1 | 2/2009 | |
| WO | WO 2012/138820 * | 10/2012 | ............ B29C 44/00 |
| WO | 2012157851 A2 | 11/2012 | |
| WO | 2019134764 A1 | 7/2019 | |
| WO | 2020147211 A1 | 7/2020 | |

OTHER PUBLICATIONS

International Search Report and Written Opinion; Application Ser. No. PCT/CN2020/079917; dated Jun. 24, 2020; 10 pages.
U.S. Appl. No. 17/073,586, filed Oct. 19, 2020, to Hongsing Tan et al.
All Office Actions, U.S. Appl. No. 17/239,799.
All Office Actions; U.S. Appl. No. 17/073,586.

(56) References Cited

OTHER PUBLICATIONS

U.S. Appl. No. 17/239,799, filed Apr. 26, 2021, to Shufen Fan et al.
PCT Supplementary Search Report and Written Opinion for FCT/CN2020/079917 dated Aug. 2, 2021, 08 pages.

* cited by examiner (Laundry Drum)

(Laundry Impingement Oven)

MULTILAYER DISSOLVABLE SOLID ARTICLE AND METHOD OF MAKING SAME

FIELD OF THE INVENTION

The present invention relates to dissolvable solid articles comprising multiple layers of flexible, dissolvable, porous sheets, and a method of making same.

BACKGROUND OF THE INVENTION

Flexible and dissolvable sheets comprising surfactant(s) and/or other active ingredients in a water-soluble polymeric carrier or matrix are well known. Such sheets are particularly useful for delivering surfactants and/or other active ingredients upon dissolution in water. In comparison with traditional granular or liquid forms in the same product category, such sheets have better structural integrity, are more concentrated and easier to store, ship/transport, carry, and handle. In comparison with the solid tablet form in the same product category, such sheets are more flexible and less brittle, with better sensory appeal to the consumers.

In order to deliver a sufficient amount of surfactant(s) and/or other active ingredients to achieve the desired product function, it is desirable to use multiple layers of such flexible and dissolvable sheets, and it is further desirable to assemble such multiple layers into a unitary dissolvable solid article, which can then be sold as a unitary finished product.

Various challenges may be encountered when trying to assemble multiple layers of these flexible and dissolvable sheets into a unitary article. First, such a multilayer structure may suffer from significantly slower dissolution rate in water, in comparison with a single layer structure. Second, it may be necessary to apply adhesives or binders between adjacent layers in order to ensure sufficient bonding of such adjacent layers, which is critical for the overall structural integrity of the multilayer structure. Such adhesives/binders and their application processes will not only lead to significant increase in the manufacturing costs and processing complexity, but also will slow down dissolution of the multilayer structure in water and further exacerbate the existing dissolution problem.

Therefore, there is a need for a multilayer structure with improved dissolution rate and sufficient bonding strength between adjacent flexible and dissolvable layers, but which is essentially free of adhesives.

It will also be advantageous to develop a cost-effective and readily scalable process for making the above-mentioned multilayer structure.

SUMMARY OF THE INVENTION

The present invention provides a multilayer dissolvable solid article, which comprises two or more flexible, dissolvable, porous sheets that have self-adhering properties.

Specifically, each of said two or more sheets in the dissolvable solid article of the present invention comprises a water-soluble polymer and a surfactant and is characterized by a Percent Open Cell Content of from about 80% to 100%, preferably from about 85% to 100%, more preferably from about 90% to 100%, and an Overall Average Pore Size of from about 100 μm to about 2000 μm, preferably from about 150 μm to about 1000 μm, more preferably from about 200 μm to about 600 μm. The above-specified Percent Open Cell Content and Overall Average Pore Size ensure fast ingress of water into the multilayer dissolvable solid article and proper dissolution thereof in water.

At least two adjacent sheets in said article are characterized by an Adhesion Score (AdS) of no less than about 1, but the contacting surfaces of said at least adjacent sheets are essentially free of adhesives. In other words, said two adjacent sheets are capable of self-adhering, i.e., they can adhere to each other with a sufficiently strong bonding strength in between without the need for any adhesives. The AdS between the two adjacent sheets is preferably from about 1 to about 3, more preferably from about 1.5 to about 3, more preferably from about 2 to about 3, most preferably from about 2.5 and 3. More preferably, said two adjacent sheets in said article is further characterized by an Adhesion Stability Score (AdSS) of no less than about 0.5, preferably from about 0.75 to about 3, more preferably from about 1 to about 3, still more preferably from about 1.5 to about 3, still more preferably from about 2 to about 3, most preferably from about 2.5 to about 3. In a most preferred embodiment of the present invention, the entire dissolvable solid article is essentially free of adhesives.

Preferably, each of the two or more flexible, dissolvable, porous sheets is characterized by a Normalized Crystallinity of not more than about 15%, preferably not more than about 10%, more preferably not more than about 8%, still more preferably not more than about 5%, most preferably not more than about 3%. It is a surprising and unexpected discovery of the present invention that sheets characterized by a Normalized Crystallinity no more than 15% may have better self-adhering properties, in comparison with sheets characterized by a Normalized Crystallinity of higher than 15%. Therefore, it is desirable to use flexible, dissolvable, porous sheets with a relatively low Normalized Crystallinity in making the multilayer dissolvable solid article of the present invention.

Preferably, each of said two or more flexible, dissolvable, porous sheets in the above-described dissolvable solid article has opposing top and bottom surfaces, while said top surface has a Surface Average Pore Diameter that is greater than about 100 μm, preferably greater than about 110 μm, more preferably greater than about 120 μm, still more preferably greater than about 130 μm, most preferably greater than about 150 μm. More preferably, each of said sheets comprises a top region adjacent to said top surface, a bottom region adjacent to said bottom surface, and a middle region therebetween; wherein said top, middle, and bottom regions have the same thickness, and each of said top, middle and bottom regions is characterized by an Average Pore Size; and wherein the ratio of Average Pore Size in said bottom region over that in said top region is from about 0.6 to about 1.5, preferably from about 0.7 to about 1.4, preferably from about 0.8 to about 1.3, more preferably from about 1 to about 1.2. The above-specified Surface Average Pore size of the top surface and bottom-to-top Average Pore Size ratio may further facilitate ingress of water into the multilayer dissolvable solid article and correspondingly improve dissolution thereof in water.

It is also preferred that said two or more flexible, dissolvable, porous sheets in the above-described dissolvable solid article are arranged in said dissolvable solid article so that the bottom surface of a preceding sheet contacts the top surface of a following sheet. Such an arrangement may further improve adhesion between adjacent sheets.

At least one of said two or more flexible, dissolvable, porous sheets may comprise from about 5% to about 50%, preferably from about 10% to about 40%, more preferably from about 15% to about 30%, most preferably from about 20% to about 25%, of said water-soluble polymer by total weight of said sheet. Preferably, said water-soluble polymer has a weight average molecular weight of from about 50,000 to about 400,000 Daltons, more preferably from about 60,000 to about 300,000 Daltons, still more preferably from about 70,000 to about 200,000 Daltons, most preferably from about 80,000 to about 150,000 Daltons. More preferably, said water-soluble polymer is a polyvinyl alcohol (PVA) characterized by a degree of hydrolysis ranging from about 40% to 100%, preferably from about 50% to about 95%, more preferably from about 65% to about 92%, most preferably from about 70% to about 90%. Such PVA polymer may be particularly advantageous in forming a wet pre-mixture with good pore-opening and film-forming properties that are relatively independent of the type(s) of surfactant(s) incorporated thereinto.

The above-described at least one flexible, dissolvable, porous sheet may further comprise (in addition to the water-soluble polymer) from about 30% to about 90%, preferably from about 40% to about 80%, more preferably from about 50% to about 70%, of the above-mentioned surfactant by total weight of said sheet. One advantage of the multilayer dissolvable solid article of the present invention is its relatively high surfactant activity, which enables formation of concentrated/compact cleaning products with superior cleaning performance.

Preferably, each of the two or more flexible, dissolvable, porous sheets may comprise no more than about 30%, preferably from 0% to about 20%, more preferably from 0% to about 10%, most preferably from 0% to about 5%, by weight of said sheet, of unalkoxylated $C_6$-$C_{20}$ linear or branched alkyl sulfates (AS). It has been discovered, surprisingly and unexpectedly, that the presence of a significant amount of AS in the sheets of the present invention may adversely affect their self-adhering properties. Therefore, it is desirable to employ low- or nil-AS flexible, dissolvable, porous sheets in making the multilayer dissolvable solid article of the present invention.

The above-described at least one flexible, dissolvable, porous sheet may further comprise from about 0.1% to about 25%, preferably from about 0.5% to about 20%, more preferably from about 1% to about 15%, most preferably from about 2% to about 12%, of a plasticizer by total weight of said sheet. Preferably, such plasticizer is selected from the group consisting of glycerin, ethylene glycol, polyethylene glycol, propylene glycol, and combinations thereof. More preferably, such plasticizer is glycerin.

In a particularly preferred embodiment of the present invention, each of said two or more flexible, dissolvable, porous sheets is characterized by:
- an Average Cell Wall Thickness of from about 5 µm to about 200 µm, preferably from about 10 µm to about 100 µm, more preferably from about 10 µm to about 80 µm; and/or
- a final moisture content of from about 0.5% to about 25%, preferably from about 1% to about 20%, more preferably from about 3% to about 10%, by weight of said sheet; and/or
- a thickness of from about 0.5 mm to about 4 mm, preferably about 0.6 mm to about 3.5 mm, more preferably from about 0.7 mm to about 3 mm, still more preferably from about 0.8 mm to about 2 mm, most preferably from about 1 mm to about 1.5 mm; and/or
- a basis weight of from about 50 grams/m² to about 250 grams/m², preferably from about 80 grams/m² to about 220 grams/m², more preferably from about 100 grams/m² to about 200 grams/m²; and/or
- a density of from about 0.05 grams/cm³ to about 0.5 grams/cm³, preferably from about 0.06 grams/cm³ to about 0.4 grams/cm³, more preferably from about 0.07 grams/cm³ to about 0.2 grams/cm³, most preferably from about 0.08 grams/cm³ to about 0.15 grams/cm³; and/or
- a Specific Surface Area of from about 0.03 m²/g to about 0.25 m²/g, preferably from about 0.04 m²/g to about 0.22 m²/g, more preferably from about 0.05 m²/g to about 0.2 m²/g, most preferably from about 0.1 m²/g to about 0.18 m²/g.

Preferably, the dissolvable solid article of the present invention comprises from about 4 to about 50, preferably from about 5 to about 40, more preferably from about 6 to about 30, of the above-described flexible, dissolvable, porous sheets.

In another aspect, the present invention relates to a method of making a dissolvable solid article, comprising the steps of:
1) providing two or more flexible, dissolvable, porous sheets, wherein each of said two or more sheets comprises a water-soluble polymer and a surfactant; wherein each of said two or more flexible, dissolvable, porous sheets is characterized by a Percent Open Cell Content of from about 80% to 100% and an Overall Average Pore Size of from about 100 µm to about 2000 µm; and
2) arranging said two or more flexible, dissolvable, porous sheets together to form a stack; and
3) cut-sealing said stack of sheets to form the dissolvable solid article, wherein at least two adjacent sheets in said dissolvable solid article are characterized by an Adhesion Score (AdS) of no less than about 1, but the contacting surfaces of said at least two adjacent sheets are essentially free of adhesives.

Further, such method may comprise at least one of the following steps:
4) edge-sealing at least a portion of the peripheral of said dissolvable solid article;
5) perforating said dissolvable solid article to provide one or more apertures or holes that extend through all sheets of said dissolvable solid article; and
6) embossing or printing on said dissolvable solid article.

These and other aspects of the present invention will become more apparent upon reading the following detailed description of the invention.

DETAILED DESCRIPTION OF THE INVENTION

I. Definitions

Figure 1:
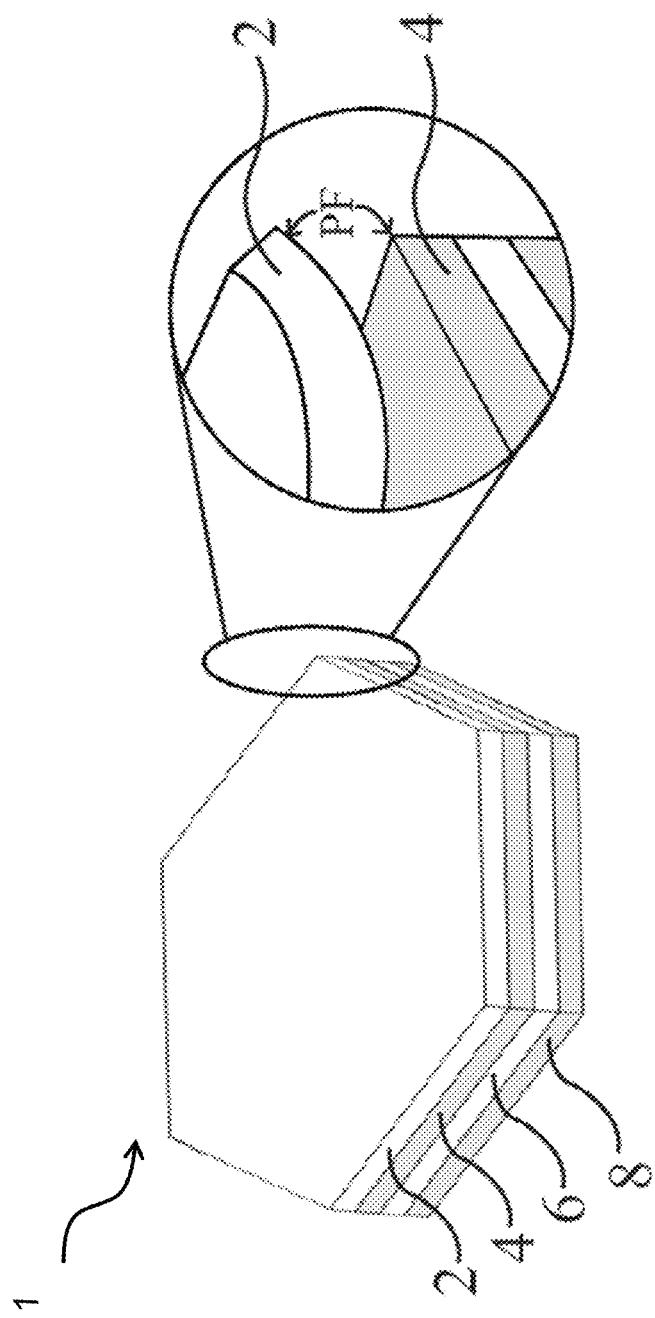
FIG. 1 shows a multilayer dissolvable solid article according to one embodiment of the present invention.

The term "dissolvable" as used herein refers to the ability of an article to completely or substantially dissolve in a sufficient amount of deionized water at 20° C. and under the atmospheric pressure within eight (8) hours without any stirring, leaving less than 5 wt % undissolved residues.

The term "solid" as used herein refers to the ability of an article to substantially retain its shape (i.e., without any visible change in its shape) at 20° C. and under the atmospheric pressure, when it is not confined and when no external force is applied thereto.

The term "flexible" as used herein refers to the ability of an article to withstand stress without breakage or significant fracture when it is bent at 90° along a center line perpendicular to its longitudinal direction. Preferably, such article can undergo significant elastic deformation and is characterized by a Young's Modulus of no more than 5 GPa, preferably no more than 1 GPa, more preferably no more than 0.5 GPa, most preferably no more than 0.2 GPa.

The term "sheet" as used herein refers to a non-fibrous structure having a three-dimensional shape, i.e., with a thickness, a length, and a width, while the length-to-thickness aspect ratio and the width-to-thickness aspect ratio are both at least about 5:1, and the length-to-width ratio is at least about 1:1. Preferably, the length-to-thickness aspect ratio and the width-to-thickness aspect ratio are both at least about 10:1, more preferably at least about 15:1, most preferably at least about 20:1; and the length-to-width aspect ratio is preferably at least about 1.2:1, more preferably at least about 1.5:1, most preferably at least about 1.618:1.

The term "water-soluble" as used herein refers to the ability of a sample material to completely dissolve in or disperse into water leaving no visible solids or forming no visibly separate phase, when at least about 25 grams, preferably at least about 50 grams, more preferably at least about 100 grams, most preferably at least about 200 grams, of such material is placed in one liter (1 L) of deionized water at 20° C. and under the atmospheric pressure with sufficient stirring.

The term "open celled foam" or "open cell pore structure" as used herein refers to a solid, interconnected, polymer-containing matrix that defines a network of spaces or cells that contain a gas, typically a gas (such as air), without collapse of the foam structure during the drying process, thereby maintaining the physical strength and cohesiveness of the solid. The interconnectivity of the structure may be described by a Percent Open Cell Content, which is measured by Test 3 disclosed hereinafter.

As used herein, the term "bottom surface" refers to a surface of the flexible, porous, dissolvable solid sheet of the present invention that is immediately contacting a supporting surface upon which the sheet of aerated wet pre-mixture is placed during the drying step, while the term "top surface" refers to a surface of said sheet that is opposite to the bottom surface. Further, such solid sheet can be divided into three (3) regions along its thickness, including a top region that is adjacent to its top surface, a bottom region that is adjacent to its bottom surface, and a middle region that is located between the top and bottom regions. The top, middle, and bottom regions are of equal thickness, i.e., each having a thickness that is about ⅓ of the total thickness of the sheet.

The term "aerate", "aerating" or "aeration" as used herein refers to a process of introducing a gas into a liquid or pasty composition by mechanical and/or chemical means.

The term "heating direction" as used herein refers to the direction along which a heat source applies thermal energy to an article, which results in a temperature gradient in such article that decreases from one side of such article to the other side. For example, if a heat source located at one side of the article applies thermal energy to said article to generate a temperature gradient that decreases from said one side to an opposing side, the heating direction is then deemed as extending from said one side to the opposing side. If both sides of such article, or different sections of such article, are heated simultaneously with no observable temperature gradient across such article, then the heating is carried out in a non-directional manner, and there is no heating direction.

The term "substantially opposite to" or "substantially offset from" as used herein refers to two directions or two lines having an offset angle of 90° or more therebetween.

The term "substantially aligned" or "substantial alignment" as used herein refers to two directions or two lines having an offset angle of less than 90° therebetween.

The term "primary heat source" as used herein refers to a heat source that provides more than 50%, preferably more than 60%, more preferably more than 70%, most preferably more than 80%, of the total thermal energy absorbed by an object (e.g., the sheet of aerated wet pre-mixture according to the present invention).

The term "controlled surface temperature" as used herein refers to a surface temperature that is relatively consistent, i.e., with less than +/−20% fluctuations, preferably less than +/−10% fluctuations, more preferably less than +/−5% fluctuations.

The term "essentially free of" or "essentially free from" means that the indicated material is at the very minimal not deliberately added to the composition or product, or preferably not present at an analytically detectable level in such composition or product. It may include compositions or products in which the indicated material is present only as an impurity of one or more of the materials deliberately added to such compositions or products.

The term "adhesive" as used herein refers to any material that exhibit adhesive property (preferably at room temperature with little or no pressure and moisture, but acceptable if at elevated temperature, under pressure and/or in the presence of moisture), which are subsequently applied to the flexible, porous, dissolvable solid sheets after they have been formed. Preferably, the adhesive is a naturally occurring or synthetic polymer. More preferably, it is different from the water-soluble polymer used in forming the flexible, porous, dissolvable solid sheet article described herein. Non-limiting examples of adhesives for practice of the present invention include hydroxyethyl cellulose, hydroxypropyl cellulose, carboxymethyl cellulose, carboxypropyl cellulose, carboxypolymethylene, polyvinylpyrrolidone, ethylene copolymers, styrene/isoprene/styrene block copolymers, copolymers of methyl vinyl ether and maleic acid anhydride, copolymers of (meth)acrylic acid alkyl esters and vinyl ester monomers, phthalate resins, polyvinyl ethers (especially dispersions thereof), polyacrylates, poly(meth) acrylates, polyesters, polyamides, polychloroprenes, polyisobutenes, polyurethanes, poloxamer, carrageenan, Veegum, carboxyvinyl polymers, natural gums (such as karaya gum, xanthan gum, guar gum, gum arabic, tragacanth gum), natural and synthetic rubbers (such as styrene/butadiene rubber, polybutene rubber, polyisoprene rubber, butyl rubber, silicone rubber, synthetic isoprene rubber), and any combinations thereof.

As mentioned hereinabove, dissolvable solid articles that each contain multiple layers of flexible and dissolvable sheets formed by incorporating surfactant(s) and/or other active ingredients into a water-soluble polymeric carrier or matrix may present several technical challenges for commercialization. First, such articles may suffer from slow dissolution during wash or even leave undissolved residues on items after wash. Second, such articles may not have the desired overall structural integrity due to weak bonding between layers. Consequently, the multiple layers may become partially or completely detached during storage or transportation. Although applying adhesives to the contacting surfaces between adjacent layers in such articles may strengthen the bonding force between layers and improve the overall structural integrity, such adhesives will inevitably increase the manufacturing cost and processing complexity. More importantly, the added adhesives may further slow down or reduce dissolution of such articles.

It has been a surprising and unexpected discovery of the present invention that dissolvable solid articles formed by stacking multiple layers of flexible, dissolvable, porous sheets of the present invention (which have an open cell foam or OCF structure defined by a Percent Open Cell Content of from about 80% to 100% and an Overall Average Pore Size of from about 100 μm to about 2000 μm) not only have a fast dissolution rate in water, but also have self-adhering properties, i.e., the adjacent sheets can self-adhere to each other with a sufficient bonding force so that no adhesive is needed. The self-adhering properties may be achieved by selectively formulating the flexible, dissolvable, porous sheets to ensure that they have a relatively low Normalized Crystallinity, and/or that the surfactants incorporated therein do not negatively affect the bonding between adjacent sheets. Correspondingly, the present invention enables formation of adhesive-free multilayer structures that are sufficiently dissolvable and structurally robust for commercialization.

Specifically, FIG. 1 shows a multilayer dissolvable solid article 1 according to the present invention, which is formed by stacking multiple layers of the above-described flexible, dissolvable, porous sheets 2, 4, 6, and 8 together. Specifically, at least two adjacent sheets 2 and 4 in said article 1 are characterized by an Adhesion Score (AdS) of no less than about 1, preferably from about 1 to about 3, preferably from about 1.5 to about 3, more preferably from about 2 to about 3, most preferably from about 2.5 to about 3, but the contacting surfaces of said at least two adjacent sheets 2 and 4 are essentially free of adhesives. More preferably, the adjacent sheets 2 and 4 are further characterized by an Adhesion Stability Score (AdSS) of no less than about 0.5, preferably from about 0.75 to about 3, more preferably from about 1 to about 3, still more preferably from about 1.5 to about 3, still more preferably from about 2 to about 3, most preferably from about 2.5 to about 3. The Adhesion Score and Adhesion Stability Score are measured according to Test Method 11 described hereinafter.

Each of the above-mentioned sheets 2, 4, 6, and 8 in the dissolvable solid article 1 of FIG. 1 comprises a water-soluble polymer and a surfactant and is characterized by a Percent Open Cell Content of from about 80% to 100%, preferably from about 85% to 100%, more preferably from about 90% to 100%, and an Overall Average Pore Size of from about 100 μm to about 2000 μm, preferably from about 150 μm to about 1000 μm, more preferably from about 200 μm to about 600 μm. Preferably, each of such flexible, dissolvable, porous sheets 2, 4, 6, and 8 is characterized by a Normalized Crystallinity of not more than about 15%, preferably not more than about 10%, more preferably not more than about 8%, still more preferably not more than about 5%, most preferably not more than about 3%.

The multilayer dissolvable solid article of the present invention may comprise any number of the above-mentioned flexible, dissolvable, porous sheets, as long as such number is no less than 2. For example, it may comprise from about 4 to about 50, preferably from about 5 to about 40, more preferably from about 6 to about 30, of said flexible, dissolvable, porous sheets. The specific OCF structures in the flexible, dissolvable, porous sheets made according to the present invention (see more detailed description hereinafter) allow stacking of many sheets (e.g., 15-40) together, while still providing a satisfactory overall dissolution rate for the stack.

The multilayer dissolvable solid article of the present invention can be of any suitable shape, either regular or irregular, e.g., spherical, cubic, rectangular, polygonal, oblong, cylindrical, rod, sheet, flower-shaped, fan-shaped, star-shaped, disc-shaped, and the like. It may be characterized by a maximum dimension D and a minimum dimension z (which is perpendicular to the maximum dimension D), while the ratio of D/z (hereinafter also referred to as the "Aspect Ratio") may range from 1 to about 10, preferably from about 1.4 to about 9, preferably from about 1.5 to about 8, more preferably from about 2 to about 7. When the Aspect Ratio is 1, the dissolvable solid article has a spherical shape. When the Aspect Ratio is about 1.4, the dissolvable solid article has a cubical shape. The multilayer dissolvable solid article of the present invention may have a minimal dimension z that is greater than about 3 mm but less than about 20 cm, preferably from about 4 mm to about 10 cm, more preferably from about 5 mm to about 30 mm.

In a particularly preferred embodiment of the present invention, the multilayer dissolvable solid article comprises from 15 to 40 layers of the above-described flexible, dissolvable, porous sheets and has an aspect ratio ranging from about 2 to about 7.

Following are detailed descriptions on the formulations and processes of making such flexible, dissolvable, porous sheets as well as the methods of assembling them into the multilayer dissolvable solid article of the present invention.

II. Overview Of Processes for Making Sheets

WO2010077627 discloses a batch process for forming porous sheets with open-celled foam (OCF) structures characterized by a Percent Open Cell Content of from about 80% to 100%, which functions to improve dissolution. Specifically, a pre-mixture of raw materials is first formed, which is vigorously aerated and then heat-dried in batches (e.g., in a convection oven or a microwave oven) to form the porous sheets with the desired OCF structures. Although such OCF structures significantly improve the dissolution rate of the resulting porous sheets, there is still a visibly denser and less porous bottom region with thicker cell walls in such sheets. Such high-density bottom region may negatively impact the flow of water through the sheets and thereby may adversely affect the overall dissolution rate of the sheets. When a plurality of such sheets is stacked together to form a multilayer structure, the "barrier" effect of multiple high-density bottom regions is especially augmented.

WO2012138820 discloses a similar process as that of WO2010077627, except that continuous drying of the aerated wet pre-mixture is achieved by using, e.g., an impingement oven (instead of a convection oven or a microwave oven). The OCF sheets formed by such a continuous drying process are characterized by improved uniformity/consistency in the pore structures across different regions thereof. Unfortunately, there are still rate-limiting factors in such OCF sheets, such as a top surface with relatively smaller pore openings and a top region with relatively smaller pores (i.e., a crust-like top region), which may negatively impact the flow of water therethrough and slow down the dissolution thereof.

During the drying step in the above-described processes, the OCF structures are formed under simultaneous mechanisms of water evaporation, bubble collapse, interstitial liquid drainage from the thin film bubble facings into the plateau borders between the bubbles (which generates openings between the bubbles and forms the open cells), and solidification of the pre-mixture. Various processing conditions may influence these mechanisms, e.g., solid content in the wet pre-mixture, viscosity of the wet pre-mixture, gravity, and the drying temperature, and the need to balance such processing conditions so as to achieve controlled drainage and form the desired OCF structures.

It has been a surprising and unexpected discovery of the present invention that the direction of thermal energy employed (i.e., the heating direction) during the drying step may also have a significant impact on the resulting OCF structures, in addition to the above-mentioned processing conditions.

For example, if the thermal energy is applied in a non-directional matter (i.e., there is no clear heating direction) during the drying step, or if the heating direction is substantially aligned with the gravitational direction (i.e., with an offset angle of less than 90° in between) during most of the drying step, the resulting flexible, porous, dissolvable solid sheet tends to have a top surface with smaller pore openings and greater pore size variations in different regions along the direction across its thickness. In contrast, when the heating direction is offset from the gravitation direction (i.e., with an offset angle of 90° or more therebetween) during most of the drying step, the resulting solid sheet may have a top surface with larger pore openings and reduced pore size variations in different regions along the direction across the thickness of such sheet. Correspondingly, the latter sheets are more receptive to water flowing through and are therefore more dissolvable than the former sheets.

While not being bound by any theory, it is believed that the alignment or misalignment between the heating direction and the gravitational direction during the drying step and the duration thereof may significantly affect the interstitial liquid drainage between the bubbles, and correspondingly impacting the pore expansion and pore opening in the solidifying pre-mixture and resulting in solid sheets with very different OCF structures. Such differences are illustrated more clearly by FIGS. 2-5 hereinafter.

Figure 2:
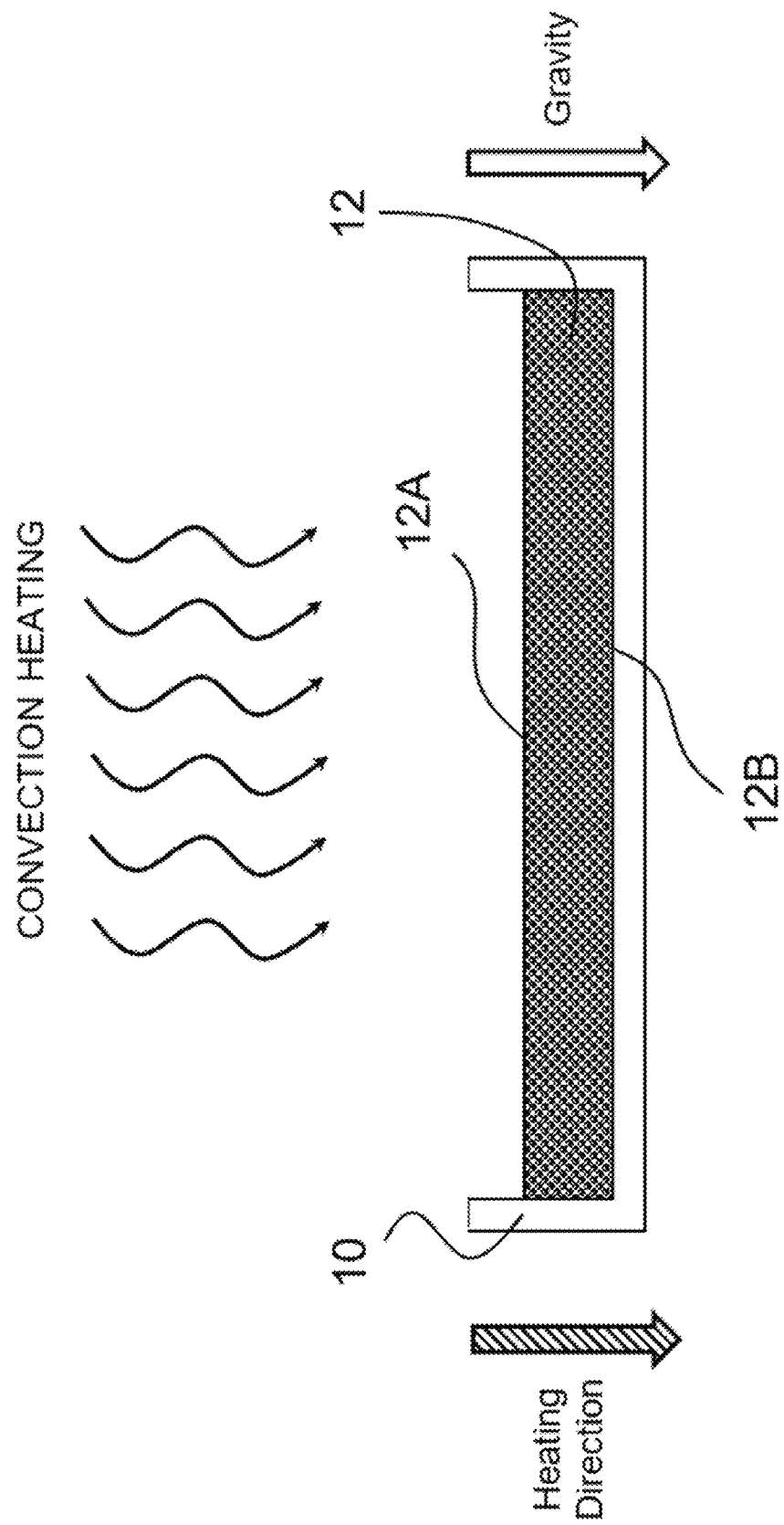
FIG. 2 shows a prior art convection-based heating/drying arrangement for making a flexible, porous, dissolvable solid sheet article in a batch process.

FIG. 2 shows a prior art convection-based heating/drying arrangement. During the drying step, a mold 10 (which can be made of any suitable materials, such as metal, ceramic or Teflon®) is filled with an aerated wet pre-mixture, which forms a sheet 12 having a first side 12A (i.e., the top side) and an opposing second side 12B (i.e., the bottom side since it is in direct contact with a supporting surface of the mold 10). Such mold 10 is placed in a 130° C. convection oven for approximately 45-46 minutes during the drying step. The convection oven heats the sheet 12 from above, i.e., along a downward heating direction (as shown by the cross-hatched arrowhead), which forms a temperature gradient in said sheet 12 that decreases from the first side 12A to the opposing second side 12B. The downward heating direction is aligned with gravitational direction (as shown by the white arrowhead), and such an aligned position is maintained throughout the entire drying time. During drying, gravity drains the liquid pre-mixture downward toward the bottom region, while the downward heating direction dries the top region first and the bottom region last. As a result, a porous solid sheet is formed with a top surface that contains numerous pores with small openings formed by gas bubbles that have not had the chance to fully expand. Such a top surface with smaller pore openings is not optimal for water ingress into the sheet, which may limit the dissolution rate of the sheet. On the other hand, the bottom region of such sheet is dense and less porous, with larger pores that are formed by fully expanded gas bubbles, but which are very few in numbers, and the cell walls between the pores in such bottom region are thick due to the downward liquid drainage effectuated by gravity. Such a dense bottom region with fewer pores and thick cell walls is a further rate-limiting factor for the overall dissolution rate of the sheet.

Figure 3:
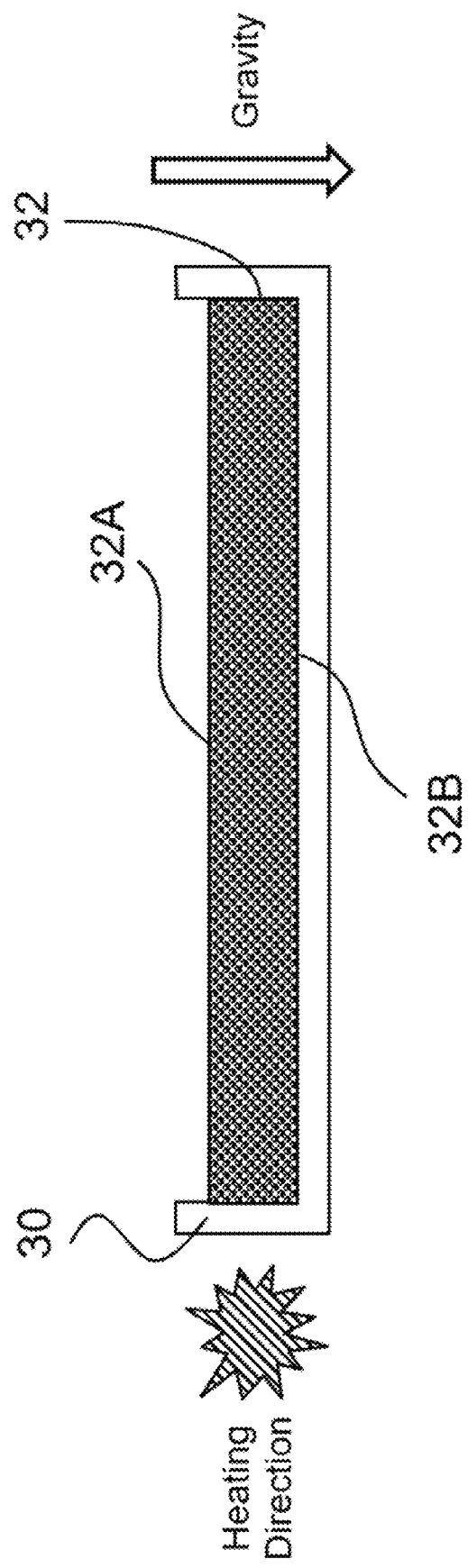
FIG. 3 shows a prior art microwave-based heating/drying arrangement for making a flexible, porous, dissolvable solid sheet article in a batch process.

FIG. 3 shows a prior art microwave-based heating/drying arrangement. During the drying step, a mold 30 is filled with an aerated wet pre-mixture, which forms a sheet 32 having a first side 32A (the top side) and an opposing second side 32B (the bottom side). Such mold 30 is then placed in a low energy density microwave applicator (not shown), which is provided by Industrial Microwave System Inc., North Carolina and operated at a power of 2.0 kW, a belt speed of 1 foot per minute and a surrounding air temperature of 54.4° C. The mold 30 is placed in such microwave application for approximately 12 minutes during the drying step. Such microwave applicator heats the sheet 32 from within, without any clear or consistent heating direction. Correspondingly, no temperature gradient is formed in said sheet 32. During drying, the entire sheet 32 is simultaneously heated, or nearly simultaneously heated, although gravity (as shown by the white arrowhead) still drains the liquid pre-mixture downward toward the bottom region. As a result, the solidified sheet so formed has more uniformly distributed and more evenly sized pores, in comparison with sheet formed by the convection-based heating/drying arrangement. However, the liquid drainage under gravity force during the microwave-based drying step may still result in a dense bottom region with thick cell walls. Further, simultaneous heating of the entire sheet 32 may still limit the pore expansion and pore opening on the top surface during the drying step, and the resulting sheet may still have a top surface with relatively smaller pore openings. Further, the microwave energy heats water within the sheet 32 and causes such water to boil, which may generate bubbles of irregular sizes and form unintended dense regions with thick cell walls.

Figure 4:
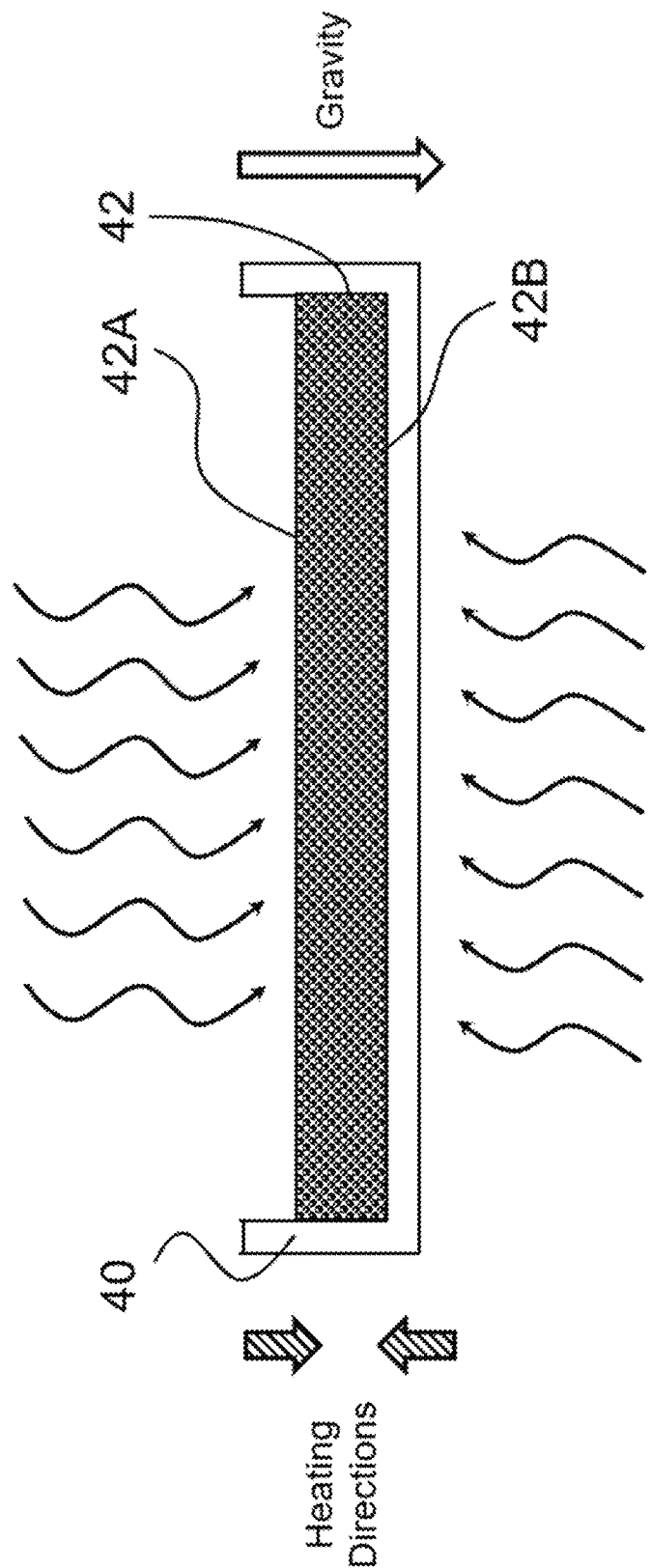
FIG. 4 shows a prior art impingement oven-based heating/drying arrangement for making a flexible, porous dissolvable solid sheet article in a continuous process.

FIG. 4 shows a prior art impingement oven-based heating/drying arrangement. During the drying step, a mold 40 is filled with an aerated wet pre-mixture, which forms a sheet 42 having a first side 42A (the top side) and an opposing second side 42B (the bottom side). Such mold 40 is then placed in a continuous impingement oven (not shown) under conditions similar to those described in Example 1, Table 2 of WO2012138820. Such continuous impingement oven heats the sheet 42 from both top and bottom at opposing and offsetting heating directions (shown by the two cross-hatched arrowheads). Correspondingly, no clear temperature gradient is formed in said sheet 42 during drying, and the entire sheet 42 is nearly simultaneously heated from both its top and bottom surfaces. Similar to the microwave-based heating/drying arrangement described in FIG. 3, gravity (as shown by the white arrowhead) continues to drain the liquid pre-mixture downward toward the bottom region in such impingement oven-based heating/drying arrangement of FIG. 4. As a result, the solidified sheet so formed has more uniformly distributed and more evenly sized pores, in comparison with sheet formed by the convection-based heating/drying arrangement. However, the liquid drainage under gravity force during the drying step may still result in a dense bottom region with thick cell walls. Further, nearly simultaneous heating of the sheet 42 from both the may still limit the pore expansion and pore opening on the top surface during the drying step, and the resulting sheet may still have a top surface with relatively smaller pore openings.

In contrast to the above-described prior art heating/drying arrangements, the present invention provides a heating/drying arrangement for drying the aerated wet pre-mixture, in which the direction of heating is purposefully configured to counteract/reduce liquid drainage caused by the gravitational force toward the bottom region (thereby reducing the density and improving pore structures in the bottom region) and to allow more time for the air bubbles near the top surface to expand during drying (thereby forming significantly larger pore openings on the top surface of the resulting sheet). Both features function to improve overall dissolution rate of the sheet and are therefore desirable.

Figure 5:
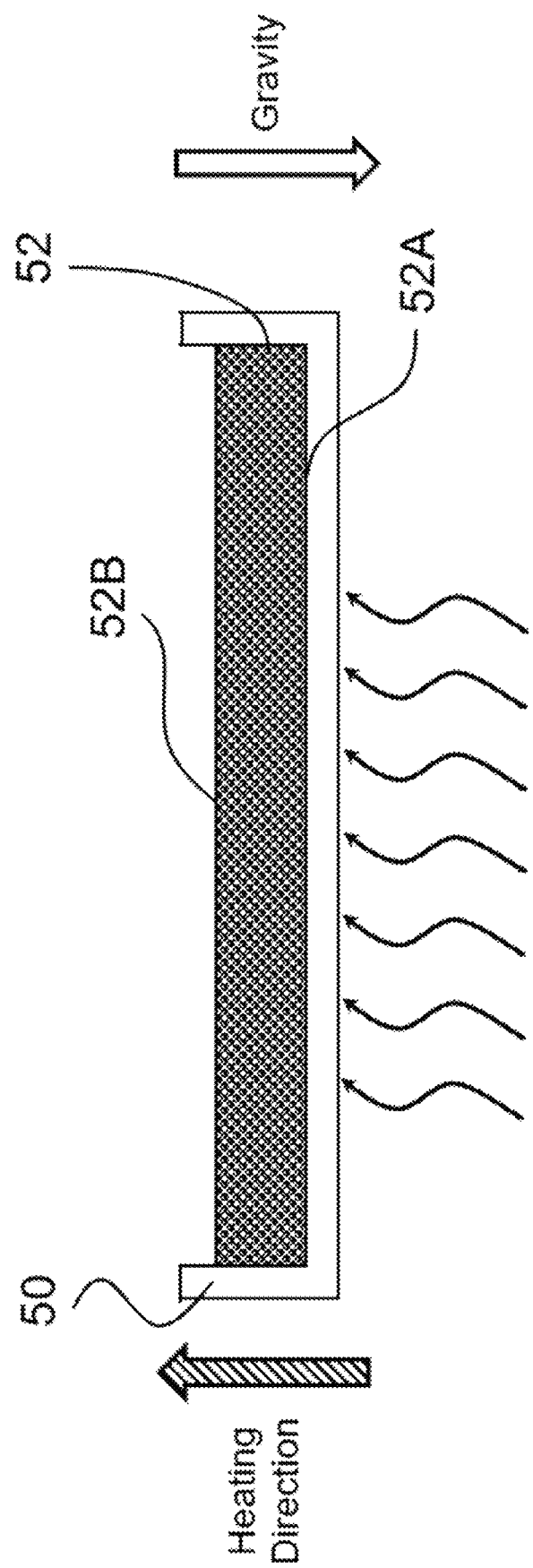
FIG. 5 shows a bottom conduction-based heating/drying arrangement for making an inventive flexible, porous, dissolvable sheet in a batch process, according to one embodiment of the present invention.

FIG. 5 shows a bottom conduction-based heating/drying arrangement for making an inventive flexible, porous, dissolvable sheet, according to one embodiment of the present invention. Specifically, a mold 50 is filled with an aerated wet pre-mixture, which forms a sheet 52 having a first side 52A (i.e., the bottom side) and an opposing second side 52B (i.e., the top side). Such mold 50 is placed on a heated surface (not shown), for example, on top of a pre-heated Peltier plate with a controlled surface temperature of about 125-130° C., for approximately 30 minutes during the drying step. Heat is conducted from the heated surface at the bottom of the mold 50 through the mold to heat the sheet 52 from below, i.e., along an upward heating direction (as shown by the cross-hatched arrowhead), which forms a temperature gradient in said sheet 52 that decreases from the first side 52A (the bottom side) to the opposing second side 52B (the top side). Such an upward heating direction is opposite to the gravitational direction (as shown by the white arrowhead), and it is maintained as so throughout the entire drying time (i.e., the heating direction is opposite to the gravitational direction for almost 100% of the drying time). During drying, the gravitational force still drains the liquid pre-mixture downward toward the bottom region. However, the upward heating direction dries the sheet from bottom up, and water vapor generated by heat at the bottom region arises upward to escape from the solidifying matrix, so the downward liquid drainage toward the bottom region is significantly limited and "counteracted"/reduced by the solidifying matrix and the uprising water vapor. Correspondingly, the bottom region of the resulting dry sheet is less dense and contains numerous pores with relatively thin cell walls. Further, because the top region is the last region that is dried during this process, the air bubbles in the top region have sufficient time to expand to form significantly larger open pores at the top surface of the resulting sheet, which are particularly effective in facilitating water ingress into the sheet. Moreover, the resulting sheet has a more evenly distributed overall pore sizes throughout different regions (e.g., top, middle, bottom) thereof.

Figure 6:
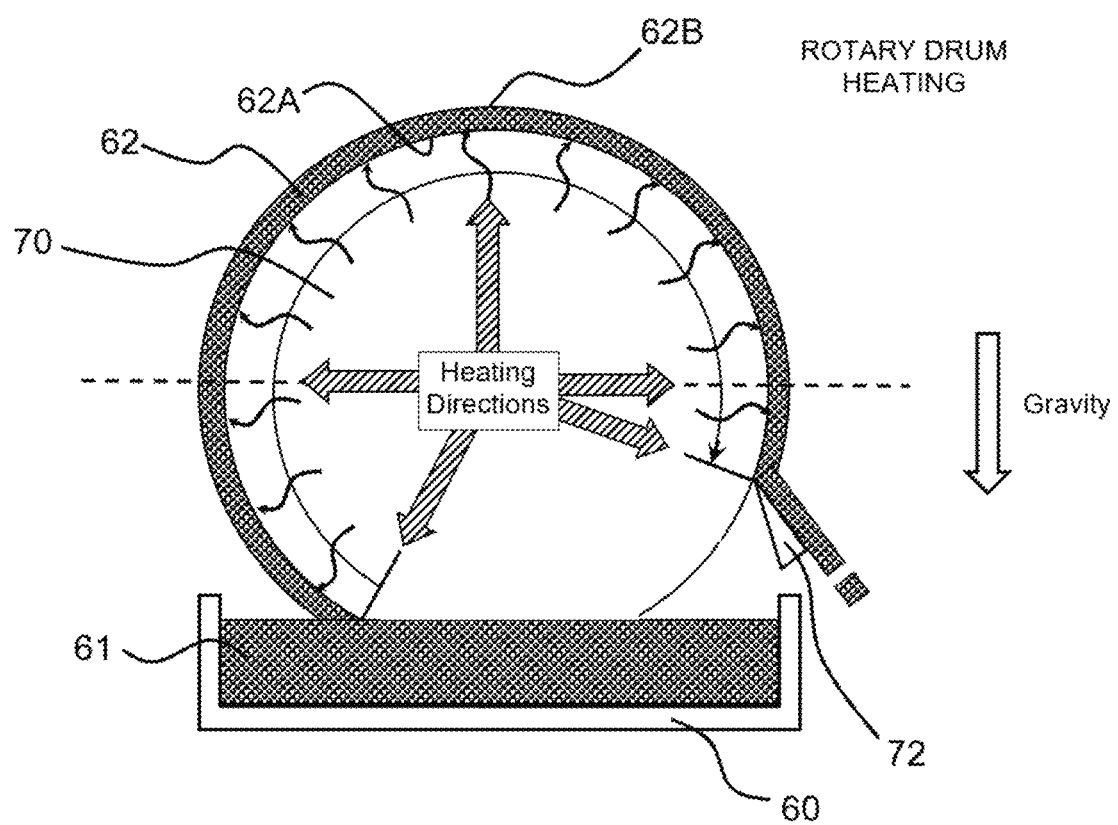
FIG. 6 shows a rotary drum-based heating/drying arrangement for making another inventive flexible, porous, dissolvable sheet in a continuous process, according to another embodiment of the present invention.

FIG. 6 shows a rotary drum-based heating/drying arrangement for making an inventive flexible, porous, dissolvable sheet, according to another embodiment of the present invention. Specifically, a feeding trough 60 is filled with an aerated wet pre-mixture 61. A heated rotatable cylinder 70 (also referred to as a drum dryer) is placed above said feeding trough 60. Said heated drum dryer 70 has a cylindrical heated outer surface characterized by a controlled surface temperature of about 130° C., and it rotates along a clock-wise direction (as shown by the thin curved line with an arrowhead) to pick up the aerated wet pre-mixture 61 from the feeding trough 60. The aerated wet pre-mixture 61 forms a thin sheet 62 over the cylindrical heated outer surface of the drum dryer 70, which rotates and dries such sheet 62 of aerated wet pre-mixture in approximately 10-15 minutes. A leveling blade (not shown) may be placed near the slurry pick-up location to ensure a consistent thickness of the sheet 62 so formed, although it is possible to control the thickness of sheet 62 simply by modulating the viscosity of the aerated wet pre-mixture 61 and the rotating speed and surface temperature of the drum dryer 70. Once dried, the sheet 62 can then picked up, either manually or by a scraper 72 at the end of the drum rotation.

As shown in FIG. 6, the sheet 62 formed by the aerated wet pre-mixture 61 comprises a first side 62A (i.e., the bottom side) that directly contacts the heated outer surface of the heated drum dryer 70 and an opposing second side 62B (i.e., the top side). Correspondingly, heat from the drum dryer 70 is conducted to the sheet 62 along an outward heating direction, to heat the first side 62A (the bottom side) of the sheet 62 first and then the opposing second side 62B (the top side). Such outward heating direction forms a temperature gradient in the sheet 62 that decreases from the first side 62A (the bottom side) to the opposing second side 62B (the top side). The outward heating direction is slowly and constantly changing as the drum dryer 70 rotates, but along a very clear and predictable path (as shown by the multiple outwardly extending cross-hatched arrowheads in FIG. 6). The relative position of the outward heating direction and the gravitational direction (as shown by the white arrowhead) is also slowing and constantly changing in a similar clear and predictable manner. For less than half of the drying time (i.e., when the heating direction is below the horizontal dashed line), the outward heating direction is substantially aligned with the gravitational direction with an offset angle of less than 90° in between. During majority of the drying time (i.e., when the heating direction is flushed with or above the horizontal dashed line), the outward heating direction is opposite or substantially opposite to the gravitational direction with an offset angle of 90° or more therebetween. Depending on the initial "start" coating position of the sheet 62, the heating direction can be opposite or substantially opposite to the gravitational direction for more than 55% of the drying time (if the coating starts at the very bottom of the drum dryer 70), preferably more than 60% of the drying time (if the coating starts at a higher position of the drum dryer 70, as shown in FIG. 6). Consequently, during most of the drying step this slowing rotating and changing heating direction in the rotary drum-based heating/drying arrangement can still function to limit and "counteract"/reduce the liquid drainage in sheet 62 caused by the gravitational force, resulting in improved OCF structures in the sheet so formed. The resulting sheet as dried by the heated drum dryer 70 is also characterized by a less dense bottom region with numerous more evenly sized pores, and a top surface with relatively larger pore openings. Moreover, the resulting sheet has a more evenly distributed overall pore sizes throughout different regions (e.g., top, middle, bottom) thereof.

In addition to employing the desired heating direction (i.e., in a substantially offset relation with respect to the gravitational direction) as mentioned hereinabove, it may also be desirable and even important to carefully adjust the viscosity and/or solid content of the wet pre-mixture, the amount and speed of aeration (air feed pump speed, mixing head speed, air flow rate, density of the aerated pre-mixture and the like, which may affect bubble sizes and quantities in the aerated pre-mixture and correspondingly impact the pore size/distribution/quantity/characteristics in the solidified sheet), the drying temperature and the drying time, in order to achieve optimal OCF structure in the resulting sheet according to the present invention.

More detailed descriptions of the processes for making the inventive flexible, porous, dissolvable sheets according to the present invention, as well as the physical and chemical characteristics of such sheets, are provided in the ensuring sections.

III. Inventive Process of Making Solid Sheets

The present invention provides a new and improved method for making flexible, porous, dissolvable solid sheets, which comprises the steps of: (a) forming a pre-mixture containing raw materials (e.g., the water-soluble polymer, active ingredients such as surfactants, and optionally a plasticizer) dissolved or dispersed in water or a suitable solvent, which is characterized by a viscosity of from about 1,000 cps to about 25,000 cps measured at about 40° C. and 1 s$^{-1}$; (b) aerating said pre-mixture (e.g., by introducing a gas into the wet slurry) to form an aerated wet pre-mixture; (c) forming said aerated wet pre-mixture into a sheet having opposing first and second sides; and (d) drying said formed sheet for a drying time of from 1 minute to 60 minutes at a temperature from 70° C. to 200° C. along a heating direction that forms a temperature gradient decreasing from the first side to the second side of said formed sheet, wherein the heating direction is substantially offset from the gravitational direction for more than half of the drying time, i.e., the drying step is conducted under heating along a mostly "anti-gravity" heating direction. Such a mostly "anti-gravity" heating direction can be achieved by various means, which include but are not limited to the bottom conduction-based heating/drying arrangement and the rotary drum-based heating/drying arrangement, as illustrated hereinabove in FIGS. 5 and 6 respectively.

Step (A): Preparation of Wet Pre-Mixture

The wet pre-mixture of the present invention is generally prepared by mixing solids of interest, including the water-soluble polymer, surfactant(s) and/or other benefit agents, optional plasticizer, and other optional ingredients, with a sufficient amount of water or another solvent in a pre-mix tank. The wet pre-mixture can be formed using a mechanical mixer. Mechanical mixers useful herein, include, but aren't limited to pitched blade turbines or MAXBLEND mixer (Sumitomo Heavy Industries).

It is particularly important in the present invention to adjust viscosity of the wet pre-mixture so that it is within a predetermined range of from about 1,000 cps to about 25,000 cps when measured at 40° C. and 1 s$^{-1}$. Viscosity of the wet pre-mixture has a significant impact on the pore expansion and pore opening of the aerated pre-mixture during the subsequent drying step, and wet pre-mixtures with different viscosities may form flexible, porous, dissolvable solid sheets of very different foam structures. On one hand, when the wet pre-mixture is too thick/viscous (e.g., having a viscosity higher than about 25,000 cps as measured at 40° C. and 1 s$^{-1}$), aeration of such wet pre-mixture may become more difficult. More importantly, interstitial liquid drainage from thin film bubble facings into the plateau borders of the three-dimensional foam during the subsequent drying step may be adversely affected or significantly limited. The interstitial liquid drainage during drying is believed to be critical for enabling pore expansion and pore opening in the aerated wet pre-mixture during the subsequent drying step. As a result, the flexible, porous, dissolvable solid sheet so formed thereby may have significantly smaller pores and less interconnectivity between the pores (i.e., more "closed" pores than open pores), which render it harder for water to ingress into and egress from such sheet. On the other hand, when the wet pre-mixture is too thin/running (e.g., having a viscosity lower than about 1,000 cps as measured at 40° C. and 1 s$^{-1}$), the aerated wet pre-mixture may not be sufficiently stable, i.e., the air bubbles may rupture, collapse, or coalescence too quickly in the wet pre-mixture after aeration and before drying. Consequently, the resulting solid sheet may be much less porous and more dense than desired.

In one embodiment, viscosity of the wet pre-mixture ranges from about 3,000 cps to about 24,000 cps, preferably from about 5,000 cps to about 23,000 cps, more preferably from about 10,000 cps to about 20,000 cps, as measured at 40° C. and 1 sec$^{-1}$. The pre-mixture viscosity values are measured using a Malvern Kinexus Lab+ rheometer with cone and plate geometry (CP1/50 SR3468 SS), a gap width of 0.054 mm, a temperature of 40° C. and a shear rate of 1.0 reciprocal seconds for a period of 360 seconds.

In a preferred but not necessary embodiment, the solids of interest are present in the wet pre-mixture at a level of from about 15% to about 70%, preferably from about 20% to about 50%, more preferably from about 25% to about 45% by total weight of said wet pre-mixture. The percent solid content is the summation of the weight percentages by weight of the total processing mixture of all solid components, semi-solid components and liquid components excluding water and any obviously volatile materials such as low boiling alcohols. On one hand, if the solid content in the wet pre-mixture is too high, viscosity of the wet pre-mixture may increase to a level that will prohibit or adversely affect interstitial liquid drainage and prevent formation of the desired predominantly open-celled porous solid structure as described herein. On the other hand, if the solid content in the wet pre-mixture is too low, viscosity of the wet pre-mixture may decrease to a level that will cause bubble rupture/collapse/coalescence and more percent (%) shrinkage of the pore structures during drying, resulting in a solid sheet that is significantly less porous and denser.

Among the solids of interest in the wet pre-mixture of the present invention, there may be present from about 1% to about 75% surfactant(s), from about 0.1% to about 25% water-soluble polymer, and optionally from about 0.1% to about 25% plasticizer, by total weight of the solids. Other actives or benefit agents can also be added into the pre-mixture.

The wet pre-mixture used for making the flexible, dissolvable, porous sheets of the present invention may have a crystallinity of not more than 15%, preferably not more than 10%, more preferably not more than 8%, still more preferably not more than 5%, most preferably not more than 3%, which is measured according to Test Method 10 hereinafter. Such a lower crystallinity of the wet pre-mixture may result in flexible, dissolvable, porous sheets with sufficient self-adhering properties, which can then be assembled into the adhesive-free multilayer dissolvable solid article of the present invention.

Optionally, the wet pre-mixture is pre-heated immediately prior to and/or during the aeration process at above ambient temperature but below any temperatures that would cause degradation of the components therein. In one embodiment, the wet pre-mixture is kept at an elevated temperature ranging from about 40° C. to about 100° C., preferably from about 50° C. to about 95° C., more preferably from about 60° C. to about 90° C., most preferably from about 75° C. to about 85° C. In one embodiment, the optional continuous heating is utilized before the aeration step. Further, additional heat can be applied during the aeration process to try and maintain the wet pre-mixture at such an elevated temperature. This can be accomplished via conductive heating from one or more surfaces, injection of steam or other processing means. It is believed that the act of pre-heating the wet pre-mixture before and/or during the aeration step may provide a means for lowering the viscosity of pre-mixtures comprising higher percent solids content for improved introduction of bubbles into the mixture and formation of the desired solid sheet. Achieving higher percent solids content is desirable since it may reduce the overall energy requirements for drying. The increase of percent solids may therefore conversely lead to a decrease in water level content and an increase in viscosity. As mentioned hereinabove, wet pre-mixtures with viscosities that are too high are undesirable for the practice of the present invention. Pre-heating may effectively counteract such viscosity increase and thus allow for the manufacture of a fast dissolving sheet even when using high solid content pre-mixtures.

Step (B): Aeration of Wet Pre-Mixture

Aeration of the wet pre-mixture is conducted in order to introduce a sufficient amount of air bubbles into the wet pre-mixture for subsequent formation of the OCF structures therein upon drying. Once sufficiently aerated, the wet pre-mixture is characterized by a density that is significantly lower than that of the non-aerated wet pre-mixture (which may contain a few inadvertently trapped air bubbles) or an insufficiently aerated wet pre-mixture (which may contain some bubbles but at a much lower volume percentage and of significantly larger bubble sizes). Preferably, the aerated wet pre-mixture has a density ranging from about 0.05 g/ml to about 0.5 g/ml, preferably from about 0.08 g/ml to about 0.4 g/ml, more preferably from about 0.1 g/ml to about 0.35 g/ml, still more preferably from about 0.15 g/ml to about 0.3 g/ml, most preferably from about 0.2 g/ml to about 0.25 g/ml.

Aeration can be accomplished by either physical or chemical means in the present invention. In one embodiment, it can be accomplished by introducing a gas into the wet pre-mixture through mechanical agitation, for example, by using any suitable mechanical processing means, including but not limited to: a rotor stator mixer, a planetary mixer, a pressurized mixer, a non-pressurized mixer, a batch mixer, a continuous mixer, a semi-continuous mixer, a high shear mixer, a low shear mixer, a submerged sparger, or any combinations thereof In another embodiment, it may be achieved via chemical means, for example, by using chemical foaming agents to provide in-situ gas formation via chemical reaction of one or more ingredients, including formation of carbon dioxide ($CO_2$ gas) by an effervescent system.

In a particularly preferred embodiment, it has been discovered that the aeration of the wet pre-mixture can be cost-effectively achieved by using a continuous pressurized aerator or mixer that is conventionally utilized in the foods industry in the production of marshmallows. Continuous pressurized mixers may work to homogenize or aerate the wet pre-mixture to produce highly uniform and stable foam structures with uniform bubble sizes. The unique design of the high shear rotor/stator mixing head may lead to uniform bubble sizes in the layers of the open celled foam. Suitable continuous pressurized aerators or mixers include the Morton whisk (Morton Machine Co., Motherwell, Scotland), the Oakes continuous automatic mixer (E.T. Oakes Corporation, Hauppauge, New York), the Fedco Continuous Mixer (The Peerless Group, Sidney, Ohio), the Mondo (Haas-Mondomix B. V., Netherlands), the Aeros (Aeros Industrial Equipment Co., Ltd., Guangdong Province, China), and the Preswhip (Hosokawa Micron Group, Osaka, Japan). For example, an Aeros A20 continuous aerator can be operated at a feed pump speed setting of about 300-800 (preferably at about 500-700) with a mixing head speed setting of about 300-800 (preferably at about 400-600) and an air flow rate of about 50-150 (preferably 60-130, more preferably 80-120) respectively. For another example, an Oakes continuous automatic mixer can be operated at a mixing head speed setting of about 10-30 rpm (preferably about 15-25 rpm, more preferably about 20 rpm) with an air flow rate of about 10-30 Litres per hour (preferably about 15-25 L/hour, more preferably about 19-20 L/hour).

In another specific embodiment, aeration of the wet pre-mixture can be achieved by using the spinning bar that is a part of the rotary drum dryer, more specifically a component of the feeding trough where the wet pre-mixture is stored before it is coated onto the heated outer surface of the drum dryer and dried. The spinning bar is typically used for stirring the wet pre-mixture to preventing phase separation or sedimentation in the feeding trough during the waiting time before it is coated onto the heated rotary drum of the drum dryer. In the present invention, it is possible to operate such spinning bar at a rotating speed ranging from about 150 to about 500 rpm, preferably from about 200 to about 400 rpm, more preferably from about 250 to about 350 rpm, to mix the wet pre-mixture at the air interface and provide sufficient mechanical agitation needed for achieving the desired aeration of the wet pre-mixture.

As mentioned hereinabove, the wet pre-mixture can be maintained at an elevated temperature during the aeration process, so as to adjust viscosity of the wet pre-mixture for optimized aeration and controlled draining during drying. For example, when aeration is achieved by using the spinning bar of the rotary drum, the aerated wet pre-mixture in the feeding trough is typically maintained at about 60° C. during initial aeration by the spinning bar (while the rotary drum is stationary), and then heated to about 70° C. when the rotary drum is heated up and starts rotating.

Bubble size of the aerated wet pre-mixture assists in achieving uniform layers in the OCF structures of the resulting solid sheet. In one embodiment, the bubble size of the aerated wet pre-mixture is from about 5 to about 100 microns; and in another embodiment, the bubble size is from about 20 microns to about 80 microns. Uniformity of the bubble sizes causes the resulting solid sheets to have consistent densities.

Step (C): Sheet-Forming

After sufficient aeration, the aerated wet pre-mixture forms one or more sheets with opposing first and second sides. The sheet-forming step can be conducted in any suitable manners, e.g., by extrusion, casting, molding, vacuum-forming, pressing, printing, coating, and the like. More specifically, the aerated wet pre-mixture can be formed into a sheet by: (i) casting it into shallow cavities or trays or specially designed sheet moulds; (ii) extruding it onto a continuous belt or screen of a dryer; (iii) coating it onto the outer surface of a rotary drum dryer. Preferably, the supporting surface upon which the sheet is formed is formed by or coated with materials that are anti-corrosion, non-interacting and/or non-sticking, such as metal (e.g., steel, chromium, and the like), TEFLON®, polycarbonate, NEOPRENE®, HDPE, LDPE, rubber, glass and the like.

Preferably, the formed sheet of aerated wet pre-mixture has a thickness ranging from a thickness ranging from 0.5 mm to 4 mm, preferably from 0.6 mm to 3.5 mm, more preferably from 0.7 mm to 3 mm, still more preferably from 0.8 mm to 2 mm, most preferably from 0.9 mm to 1.5 mm. Controlling the thickness of such formed sheet of aerated wet pre-mixture may be important for ensuring that the resulting solid sheet has the desired OCF structures. If the formed sheet is too thin (e.g., less than 0.5 mm in thickness), many of the air bubbles trapped in the aerated wet pre-mixture will expand during the subsequent drying step to form through-holes that extend through the entire thickness of the resulting solid sheet. Such through-holes, if too many, may significantly compromise both the overall structural integrity and aesthetic appearance of the sheet. If the formed sheet is too thick, not only it will take longer to dry, but also it will result in a solid sheet with greater pore size variations between different regions (e.g., top, middle, and bottom regions) along its thickness, because the longer the drying time, the more imbalance of forces may occur through bubble rupture/collapse/coalescence, liquid drainage, pore expansion, pore opening, water evaporation, and the like. More importantly, it is easier to assembly multiple layers of relatively thin sheets into the multilayer structures of the present invention, while still providing satisfactory pore structures for fast dissolution as well as ensuring efficient drying within a relatively short drying time.

Step (D): Drying Under Anti-Gravity Heating

A key feature of the present invention is the use of an anti-gravity heating direction during the drying step, either through the entire drying time or at least through more than half of the drying time. Without being bound by any theory, it is believed that such anti-gravity heating direction may reduce or counteract excessive interstitial liquid drainage toward the bottom region of the formed sheet during the drying step. Further, because the top surface is dried last, it allows longer time for air bubbles near the top surface of the formed sheet to expand and form pore openings on the top surface (because once the wet matrix is dried, the air bubbles can no longer expand or form surface openings). Consequently, the solid sheet formed by drying with such anti-gravity heating is characterized by improved OCF structures that enables faster dissolution as well as other surprising and unexpected benefits.

In a specific embodiment, the anti-gravity heating direction is provided by a conduction-based heating/drying arrangement, either the same or similar to that illustrated by FIG. 5. For example, the aerated wet pre-mixture can be casted into a mold to form a sheet with two opposing sides. The mold can then be placed on a hot plate or a heated moving belt or any other suitable heating device with a planar heated surface characterized by a controlled surface temperature of from about 80° C. to about 170° C., preferably from about 90° C. to about 150° C., more preferably from about 100° C. to about 140° C. Thermal energy is transferred from the planar heated surface to the bottom surface of the sheet of aerated wet pre-mixture via conduction, so that solidification of the sheet starts with the bottom region and gradually moves upward to reach the top region last. In order to ensure that the heating direction is primarily anti-gravity (i.e., substantially offset from the gravitational direction) during this process, it is preferred that the heated surface is a primary heat source for said sheet during drying. If there are any other heating sources, the overall heating direction may change accordingly. More preferably, the heated surface is the only heat source for said sheet during drying.

In another specific embodiment, the anti-gravity heating direction is provided by a rotary drum-based heating/drying arrangement, which is also referred to as drum drying or roller drying, similar to that illustrated in FIG. 6. Drum drying is one type of contact-drying methods, which is used for drying out liquids from a viscous pre-mixture of raw materials over the outer surface of a heated rotatable drum (also referred to as a roller or cylinder) at relatively low temperatures to form sheet-like articles. It is a continuous drying process particularly suitable for drying large volumes. Because the drying is conducted at relatively low temperatures via contact-heating/drying, it normally has high energy efficiency and does not adversely affect the compositional integrity of the raw materials.

The heated rotatable cylinder used in drum drying is heated internally, e.g., by steam or electricity, and it is rotated by a motorized drive installed on a base bracket at a predetermined rotational speed. The heated rotatable cylinder or drum preferably has an outer diameter ranging from about 0.5 meters to about 10 meters, preferably from about 1 meter to about 5 meters, more preferably from about 1.5 meters to about 2 meters. It may have a controlled surface temperature of from about 80° C. to about 170° C., preferably from about 90° C. to about 150° C., more preferably from about 100° C. to about 140° C. Further, such heated rotatable cylinder is rotating at a speed of from about 0.005 rpm to about 0.25 rpm, preferably from about 0.05 rpm to about 0.2 rpm, more preferably from about 0.1 rpm to about 0.18 rpm.

Said heated rotatable cylinder is preferably coated with a non-stick coating on its outer surface. The non-stick coating may be overlying on the outer surface of the heated rotatable drum, or it can be fixed to a medium of the outer surface of the heated rotatable drum. The medium includes, but is not limited to, heat-resisting non-woven fabrics, heat-resisting carbon fiber, heat-resisting metal or non-metallic mesh and the like. The non-stick coating can effectively preserve structural integrity of the sheet-like article from damage during the sheet-forming process.

There is also provided a feeding mechanism on the base bracket for adding the aerated wet pre-mixture of raw materials as described hereinabove onto the heated rotatable drum, thereby forming a thin layer of the viscous pre-mixture onto the outer surface of the heated rotatable drum. Such thin layer of the pre-mixture is therefore dried by the heated rotatable drum via contact-heating/drying. The feeding mechanism includes a feeding trough installed on the base bracket, while said feeding trough has installed thereupon at least one (preferably two) feeding hopper(s), an imaging device for dynamic observation of the feeding, and an adjustment device for adjusting the position and inclination angle of the feeding hopper. By using said adjustment device to adjust the distance between said feeding hopper and the outer surface of the heated rotatable drum, the need for different thicknesses of the formed sheet-like article can be met. The adjustment device can also be used to adjust the feeding hopper to different inclination angles so as to meet the material requirements of speed and quality. The feeding trough may also include a spinning bar for stirring the wet pre-mixture therein to avoid phase separation and sedimentation before the wet pre-mixture is coated onto the outer surface of the heated rotatable cylinder. Such spinning bar, as mentioned hereinbefore, can also be used to aerate the wet pre-mixture as needed.

There may also be a heating shield installed on the base bracket, to prevent rapid heat lost. The heating shield can also effectively save energy needed by the heated rotatable drum, thereby achieving reduced energy consumption and provide cost savings. The heating shield is a modular assembly structure, or integrated structure, and can be freely detached from the base bracket. A suction device is also installed on the heating shield for sucking the hot steam, to avoid any water condensate falling on the sheet-like article that is being formed.

There may also be an optional static scraping mechanism installed on the base bracket, for scraping or scooping up the sheet-like article already formed by the heated rotatable drum. The static scraping mechanism can be installed on the base bracket, or on one side thereof, for transporting the already formed sheet-like article downstream for further processing. The static scraping mechanism can automatically or manually move close and go away from the heated rotatable drum.

The making process of the flexible, porous, dissolvable solid structure article of the present invention is as follows. Firstly, the heated rotatable drum with the non-stick coating on the base bracket is driven by the motorized drive. Next, the adjustment device adjusts the feeding mechanism so that the distance between the feeding hopper and the outer surface of the heated rotatable drum reaches a preset value. Meanwhile, the feeding hopper adds the aerated wet pre-mixture containing all or some raw materials for making the flexible, porous, dissolvable solid structure article onto an outer surface of the heated rotatable drum, to form a thin layer of said aerated wet pre-mixture thereon with the desired thickness as described hereinabove in the preceding section. Optionally, the suction device of the heating shield sucks the hot steam generated by the heated rotatable drum. Next, the static scraping mechanism scrapes/scoops up a dried/solidified sheet, which is formed by the thin layer of aerated wet pre-mixture after it is dried by the heated rotatable drum at a relatively low temperature (e.g., 130° C.). The dried/solidified sheet can also be manually or automatically peeled off, without such static scraping mechanism and then rolled up by a roller bar.

The total drying time in the present invention depends on the formulations and solid contents in the wet pre-mixture, the drying temperature, the thermal energy influx, and the thickness of the sheet material to be dried. Preferably, the drying time is from about 1 minute to about 60 minutes, preferably from about 2 minutes to about 30 minutes, more preferably from about 2 to about 15 minutes, still more preferably from about 2 to about 10 minutes, most preferably from about 2 to about 5 minutes.

During such drying time, the heating direction is so arranged that it is substantially opposite to the gravitational direction for more than half of the drying time, preferably for more than 55% or 60% of the drying time (e.g., as in the rotary drum-based heating/drying arrangement described hereinabove), more preferably for more than 75% or even 100% of the drying time (e.g., as in the bottom conduction-based heating/drying arrangement described hereinabove).

Further, the sheet of aerated wet pre-mixture can be dried under a first heating direction for a first duration and then under a second, opposite heating direction under a second duration, while the first heating direction is substantially opposite to the gravitational direction, and while the first duration is anywhere from 51% to 99% (e.g., from 55%, 60%, 65%, 70% to 80%, 85%, 90% or 95%) of the total drying time. Such change in heating direction can be readily achieved by various other arrangements not illustrated herein, e.g., by an elongated heated belt of a serpentine shape that can rotate along a longitudinal central axis.

IV. Physical Characteristics of Inventive Solid Sheets

The flexible, porous, dissolvable solid sheets formed by the above-described processing steps are first and foremost characterized by a unique self-adhering property. Specifically, any two of such sheets can be adhered together without the need for any adhesives, and yet still achieving a sufficiently strong adhesion force as indicated by an Adhesion Score (AdS) of no less than about 1, preferably from about 1 to about 3, more preferably from about 1.5 to about 3, still more preferably from about 2 to about 3, most preferably from about 2.5 to about 3. Further, such adhesion force may be strong enough to withstand external mechanical force (e.g., the force exerted by a drop test), as indicated by an Adhesion Stability Score (AdSS) of no less than about 0.5, preferably from about 0.75 to about 3, more preferably from about 1 to about 3, still more preferably from about 1.5 to about 3, still more preferably from about 2 to about 3, most preferably from about 2.5 to about 3.

It has been a surprising and unexpected discovery of the present invention that flexible, dissolvable, porous sheets characterized by a Normalized Crystallinity of no more than 15% may have better self-adhering properties, in comparison with similar sheets characterized by a Normalized Crystallinity of higher than 15%. Therefore, it is desirable to use sheets with a relatively low Normalized Crystallinity. Preferably, each of the flexible, dissolvable, porous sheets employed by the present invention in making in making the multilayer dissolvable solid article is characterized by a Normalized Crystallinity of not more than about 15%, preferably not more than about 10%, more preferably not more than about 8%, still more preferably not more than about 5%, most preferably not more than about 3%.

The flexible, porous, dissolvable solid sheet employed by the present invention is also characterized by improved pore structures, which are achieved by using the inventive processes as described hereinabove and which allow easier water ingress into the sheet and faster dissolution of the sheet in water. In general, such solid sheet may be characterized by: (i) a Percent Open Cell Content of from about 80% to 100%, preferably from about 85% to 100%, more preferably from about 90% to 100%, as measured by the Test 3 hereinafter; and (ii) an Overall Average Pore Size of from about 100 μm to about 2000 μm, preferably from about 150 μm to about 1000 μm, more preferably from about 200 μm to about 600 μm, as measured by the Micro-CT method described in Test 2 hereinafter. The Overall Average Pore Size defines the porosity of the OCF structure of the present invention. The Percent Open Cell Content defines the interconnectivity between pores in the OCF structure of the present invention. Interconnectivity of the OCF structure may also be described by a Star Volume or a Structure Model Index (SMI) as disclosed in WO2010077627 and WO2012138820.

Such solid sheet of the present invention has opposing top and bottom surfaces, while its top surface may be characterized by a Surface Average Pore Diameter that is greater than about 100 µm, preferably greater than about 110 µm, preferably greater than about 120 µm, more preferably greater than about 130 µm, most preferably greater than about 150 µm, as measured by the SEM method described in Test 1 hereinafter. When comparing with solid sheets formed by prior art heating/drying arrangements (e.g., the convection-based, the microwave-based, or the impingement oven-based arrangements), the solid sheet formed by the inventive heating/drying arrangement of the present invention has a significantly larger Surface Average Pore Diameter at its top surface (as demonstrated by FIGS. 7A-7B, which are described in detail in Example 1 hereinafter), because under the specifically arranged directional heating of the present invention, the top surface of the formed sheet of aerated wet pre-mixture is the last to dry/solidify, and the air bubbles near the top surface has the longest time to expand and form larger pore openings at the top surface.

Still further, the solid sheet formed by the inventive heating/drying arrangement of the present invention is characterized by a more uniform pore size distribution between different regions along its thickness direction, in comparison with the sheets formed by prior art heating/drying arrangements. Specifically, the solid sheet of the present invention comprises a top region adjacent to the top surface, a bottom region adjacent to the bottom surface, and a middle region therebetween, while the top, middle, and bottom regions all have the same thickness. Each of the top, middle and bottom regions of such solid sheet is characterized by an Average Pore Size, while the ratio of Average Pore Size in the bottom region over that in the top region (i.e., bottom-to-top Average Pore Size ratio) is from about 0.6 to about 1.5, preferably from about 0.7 to about 1.4, preferably from about 0.8 to about 1.3, more preferably from about 1 to about 1.2. In comparison, a solid sheet formed by a prior art impingement oven-based heating/drying arrangement may have a bottom-to-top Average Pore Size ratio of more than 1.5, typically about 1.7-2.2 (as demonstrated in Example 1 hereinafter). Moreover, the solid sheet of the present invention may be characterized by a bottom-to-middle Average Pore Size ratio of from about 0.5 to about 1.5, preferably from about 0.6 to about 1.3, more preferably from about 0.8 to about 1.2, most preferably from about 0.9 to about 1.1, and a middle-to-top Average Pore Size ratio of from about 1 to about 1.5, preferably from about 1 to about 1.4, more preferably from about 1 to about 1.2.

Still further, the relative standard deviation (RSTD) between Average Pore Sizes in the top, middle and bottom regions of the solid sheet of the present invention is no more than 20%, preferably no more than 15%, more preferably no more than 10%, most preferably no more than 5%. In contrast, a solid sheet formed by a prior art impingement oven-based heating/drying arrangement may have a relative standard deviation (RSTD) between top/middle/bottom Average Pore Sizes of more than 20%, likely more than 25% or even more than 35% (as demonstrated in Example 1 hereinafter).

Preferably, the solid sheet of the present invention is further characterized by an Average Cell Wall Thickness of from about 5 µm to about 200 µm, preferably from about 10 µm to about 100 µm, more preferably from about 10 µm to about 80 µm, as measured by Test 2 hereinafter.

The solid sheet of the present invention may contain a small amount of water. Preferably, it is characterized by a final moisture content of from 0.5% to 25%, preferably from 1% to 20%, more preferably from 3% to 10%, by weight of said solid sheet, as measured by Test 4 hereinafter. An appropriate final moisture content in the resulting solid sheet may ensure the desired flexibility/deformability of the sheet, as well as providing soft/smooth sensory feel to the consumers. If the final moisture content is too low, the sheet may be too brittle or rigid. If the final moisture content is too high, the sheet may be too sticky, and its overall structural integrity may be compromised.

The solid sheet of the present invention may have a thickness ranging from about 0.6 mm to about 3.5 mm, preferably from about 0.7 mm to about 3 mm, more preferably from about 0.8 mm to about 2 mm, most preferably from about 1 mm to about 1.5 mm. Thickness of the solid sheet can be measured using Test 5 described hereinafter. The solid sheet after drying may be slightly thicker than the sheet of aerated wet pre-mixture, due to pore expansion that in turn leads to overall volume expansion.

The solid sheet of the present invention may further be characterized by a basis weight of from about 50 grams/m$^2$ to about 250 grams/m$^2$, preferably from about 80 grams/m$^2$ to about 220 grams/m$^2$, more preferably from about 100 grams/m$^2$ to about 200 grams/m$^2$, as measured by Test 6 described hereinafter.

Still further, the solid sheet of the present invention may have a density ranging from about 0.05 grams/cm$^3$ to about 0.5 grams/cm$^3$, preferably from about 0.06 grams/cm$^3$ to about 0.4 grams/cm$^3$, more preferably from about 0.07 grams/cm$^3$ to about 0.2 grams/cm$^3$, most preferably from about 0.08 grams/cm$^3$ to about 0.15 grams/cm$^3$, as measured by Test 7 hereinafter. Density of the solid sheet of the present invention is lower than that of the sheet of aerated wet pre-mixture, also due to pore expansion that in turn leads to overall volume expansion.

Furthermore, the solid sheet of the present invention can be characterized by a Specific Surface Area of from about 0.03 m$^2$/g to about 0.25 m$^2$/g, preferably from about 0.04 m$^2$/g to about 0.22 m$^2$/g, more preferably from 0.05 m$^2$/g to 0.2 m$^2$/g, most preferably from 0.1 m$^2$/g to 0.18 m$^2$/g, as measured by Test 8 described hereinafter. The Specific Surface Area of the solid sheet of the present invention may be indicative of its porosity and may impact its dissolution rate, e.g., the greater the Specific Surface Area, the more porous the sheet and the faster its dissolution rate.

V. Formulations of Inventive Solid Sheets

1. Water-soluble Polymer

As mentioned hereinabove, the flexible, porous, dissolvable solid sheet of the present invention may be formed by a wet pre-mixture that comprises a water-soluble polymer. Such a water-soluble polymer may function in the resulting solid sheet as a film-former, a structurant as well as a carrier for other active ingredients (e.g., surfactants, emulsifiers, builders, chelants, perfumes, colorants, and the like). Preferably, the wet pre-mixture may comprise from about 3% to about 20% by weight of the pre-mixture of water-soluble polymer, in one embodiment from about 5% to about 15% by weight of the pre-mixture of water-soluble polymer, in one embodiment from about 7% to about 10% by weight of the pre-mixture of water-soluble polymer.

After drying, it is preferred that the water-soluble polymer is present in the flexible, porous, dissolvable solid sheet of the present invention in an amount ranging from about 10% to about 40%, preferably from about 15% to about 30%, more preferably from about 20% to about 25%, by total weight of the solid sheet. In a particularly preferred embodiment of the present invention, the total amount of water-soluble polymer(s) present in the flexible, porous, dissolvable solid sheet of the present invention is no more than 25% by total weight of such article.

Water-soluble polymers suitable for the practice of the present invention may be selected those with weight average molecular weights ranging from about 50,000 to about 400,000 Daltons, preferably from about 60,000 to about 300,000 Daltons, more preferably from about 70,000 to about 200,000 Daltons, most preferably from about 80,000 to about 150,000 Daltons. The weight average molecular weight is computed by summing the average molecular weights of each polymer raw material multiplied by their respective relative weight percentages by weight of the total weight of polymers present within the porous solid. The weight average molecular weight of the water-soluble polymer used herein may impact the viscosity of the wet premixture, which may in turn influence the bubble number and size during the aeration step as well as the pore expansion/opening results during the drying step. Further, the weight average molecular weight of the water-soluble polymer may affect the overall film-forming properties of the wet premixture and its compatibility/incompatibility with certain surfactants.

The water-soluble polymers of the present invention may include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymers of the present invention may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers can also be used as water-soluble polymers in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

The water-soluble polymer of the present invention may include starch. As used herein, the term "starch" include both naturally occurring or modified starches. Typical natural sources for starches can include cereals, tubers, roots, legumes and fruits. More specific natural sources can include corn, pea, potato, banana, barley, wheat, rice, sago, amaranth, tapioca, arrowroot, canna, sorghum, and waxy or high amylase varieties thereof. The natural starches can be modified by any modification method known in the art to form modified starches, including physically modified starches, such as sheared starches or thermally-inhibited starches; chemically modified starches, such as those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Preferred water-soluble polymers of the present invention include polyvinyl alcohols, polyvinylpyrrolidones, polyalkylene oxides, starch and starch derivatives, pullulan, gelatin, hydroxypropylmethylcelluloses, methylcelluloses, and carboxymethycelluloses. More preferred water-soluble polymers of the present invention include polyvinyl alcohols, and hydroxypropylmethylcelluloses.

Most preferred water-soluble polymers of the present invention are polyvinyl alcohols characterized by a degree of hydrolysis ranging from about 40% to about 100%, preferably from about 50% to about 95%, more preferably from about 70% to about 92%, most preferably from about 80% to about 90%. Commercially available polyvinyl alcohols include those from Celanese Corporation (Texas, USA) under the CELVOL trade name including, but not limited to, CELVOL 523, CELVOL 530, CELVOL 540, CELVOL 518, CELVOL 513, CELVOL 508, CELVOL 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China); and combinations thereof. In a particularly preferred embodiment of the present invention, the flexible, porous, dissolvable solid sheet comprises from about 10% to about 25%, more preferably from about 15% to about 23%, by total weight of such article, of a polyvinyl alcohol having a weight average molecular weight ranging from 80,000 to about 150,000 Daltons and a degree of hydrolysis ranging from about 80% to about 90%.

In addition to polyvinyl alcohols as mentioned hereinabove, a single starch or a combination of starches may be used as a filler material in such an amount as to reduce the overall level of water-soluble polymers required, so long as it helps provide the solid sheet with the requisite structure and physical/chemical characteristics as described herein. However, too much starch may comprise the solubility and structural integrity of the sheet. Therefore, in preferred embodiments of the present invention, it is desired that the solid sheet comprises no more than 20%, preferably from 0% to 10%, more preferably from 0% to 5%, most preferably from 0% to 1%, by weight of said solid sheet, of starch.

2. Surfactants

In addition to the water-soluble polymer described hereinabove, the solid sheet article of the present invention comprises one or more surfactants. The surfactants may function as emulsifying agents during the aeration process to create a sufficient amount of stable bubbles for forming the desired OCF structure of the present invention. Further, the surfactants may function as active ingredients for delivering a desired cleansing benefit.

In a preferred embodiment of the present invention, the solid sheet comprises one or more surfactants selected from the group consisting of anionic surfactants, nonionic surfactants, cationic surfactants, zwitterionic surfactants, amphoteric surfactants, polymeric surfactants or combinations thereof. Depending on the desired application of such solid sheet and the desired consumer benefit to be achieved, different surfactants can be selected. One benefit of the present invention is that the OCF structures of the solid sheet allow for incorporation of a high surfactant content while still providing fast dissolution. Consequently, highly concentrated cleansing compositions can be formulated into the solid sheets of the present invention to provide a new and superior cleansing experience to the consumers.

The surfactant as used herein may include both surfactants from the conventional sense (i.e., those providing a consumer-noticeable lathering effect) and emulsifiers (i.e., those that do not provide any lathering performance but are intended primarily as a process aid in making a stable foam structure). Examples of emulsifiers for use as a surfactant component herein include mono- and di-glycerides, fatty alcohols, polyglycerol esters, propylene glycol esters, sorbitan esters and other emulsifiers known or otherwise commonly used to stabilize air interfaces.

The total amount of surfactants present in the solid sheet article of the present invention may range widely from about 5% to about 80%, preferably from about 10% to about 70%, more preferably from about 30% to about 65%, by total weight of said solid sheet article. Correspondingly, the wet pre-mixture may comprise from about 1% to about 40% by weight of the wet pre-mixture of surfactant(s), in one embodiment from about 2% to about 35% by weight of the wet pre-mixture of surfactant(s), in one embodiment from about 5% to about 30% by weight of the wet pre-mixture of surfactant(s).

In a preferred embodiment of the present invention, the solid sheet article of the present invention is a cleansing product containing from about 30% to about 90%, preferably from about 40% to about 80%, more preferably from about 50% to about 70%, of one or more surfactants by total weight of said solid sheet article. In such cases, the wet pre-mixture may comprise from about 10% to about 40% by weight of the wet pre-mixture of surfactant(s), in one embodiment from about 12% to about 35% by weight of the wet pre-mixture of surfactant(s), in one embodiment from about 15% to about 30% by weight of the wet pre-mixture of surfactant(s).

Suitable anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

It has been a surprising and unexpected discovery of the present invention that the presence of certain anionic surfactants, such as unalkoxylated $C_6$-$C_{20}$ linear or branched alkyl sulfate (AS), in the flexible, dissolvable, porous sheets may adversely affect the self-adhering properties of such sheets. Therefore, it is desirable to select and design low- or nil-AS sheets in making the multilayer dissolvable solid article of the present invention. Preferably, each of the two or more flexible, dissolvable, porous sheets may comprise no more than about 30%, preferably from 0% to about 20%, more preferably from 0% to about 10%, most preferably from 0% to about 5%, by weight of said sheet, of unalkoxylated $C_6$-$C_{20}$ linear or branched alkyl sulfates (AS).

One category of anionic surfactants particularly suitable for practice of the present invention include $C_6$-$C_{20}$ linear alkylbenzene sulphonate (LAS) surfactant. LAS surfactants are well known in the art and can be readily obtained by sulfonating commercially available linear alkylbenzenes. Exemplary $C_{10}$-$C_{20}$ linear alkylbenzene sulfonates that can be used in the present invention include alkali metal, alkaline earth metal or ammonium salts of $C_{10}$-$C_{20}$ linear alkylbenzene sulfonic acids, and preferably the sodium, potassium, magnesium and/or ammonium salts of $C_{11}$-$C_{18}$ or $C_{11}$-$C_{14}$ linear alkylbenzene sulfonic acids. More preferred are the sodium or potassium salts of $C_{12}$ and/or $C_{14}$ linear alkylbenzene sulfonic acids, and most preferred is the sodium salt of $C_{12}$ and/or $C_{14}$ linear alkylbenzene sulfonic acid, i.e., sodium dodecylbenzene sulfonate or sodium tetradecylbenzene sulfonate.

LAS provides superior cleaning benefit and is especially suitable for use in laundry detergent applications. More importantly, the presence of LAS does not adversely affect the self-adhering properties of the resulting sheets, unlike AS. However, conventional wisdom has taught to use AS as the main surfactant in forming the sheets, due to limitations imparted by the sheet-forming ability of the conventional polymeric film-former or carrier. It has been a surprising and unexpected discovery of the present invention that when polyvinyl alcohol having a higher weight average molecular weight (e.g., from about 50,000 to about 400,000 Daltons, preferably from about 60,000 to about 300,000 Daltons, more preferably from about 70,000 to about 200,000 Daltons, most preferably from about 80,000 to about 150,000 Daltons) is used as the film-former and carrier, LAS can be used as a major surfactant, i.e., present in an amount that is more than 50% by weight of the total surfactant content in the solid sheet, without adversely affecting the film-forming performance and stability of the overall composition. Correspondingly, in a particular embodiment of the present invention, LAS is used as the major surfactant in the solid sheet. If present, the amount of LAS in the solid sheet of the present invention may range from about 10% to about 70%, preferably from about 20% to about 65%, more preferably from about 40% to about 60%, by total weight of the solid sheet.

Another category of anionic surfactants suitable for practice of the present invention include sodium trideceth sulfates (STS) having a weight average degree of alkoxylation ranging from about 0.5 to about 5, preferably from about 0.8 to about 4, more preferably from about 1 to about 3, most preferably from about 1.5 to about 2.5. Trideceth is a 13-carbon branched alkoxylated hydrocarbon comprising, in one embodiment, an average of at least 1 methyl branch per molecule. STS used by the present invention may be include ST(EOxPOy)S, while EOx refers to repeating ethylene oxide units with a repeating number x ranging from 0 to 5, preferably from 1 to 4, more preferably from 1 to 3, and while POy refers to repeating propylene oxide units with a repeating number y ranging from 0 to 5, preferably from 0 to 4, more preferably from 0 to 2. It is understood that a material such as ST2S with a weight average degree of ethoxylation of about 2, for example, may comprise a significant amount of molecules which have no ethoxylate, 1 mole ethoxylate, 3 mole ethoxylate, and so on, while the distribution of ethoxylation can be broad, narrow or truncated, which still results in an overall weight average degree of ethoxylation of about 2. STS is particularly suitable for personal cleansing applications, and it has been a surprising and unexpected discovery of the present invention that when polyvinyl alcohol having a higher weight average molecular weight (e.g., from about 50,000 to about 400,000 Daltons, preferably from about 60,000 to about 300,000 Daltons, more preferably from about 70,000 to about 200,000 Daltons, most preferably from about 80,000 to about 150,000 Daltons) is used as the film-former and carrier, STS can be used as a major surfactant, i.e., present in an amount that is more than 50% by weight of the total surfactant content in the solid sheet, without adversely affecting the film-forming performance and stability of the overall composition. Correspondingly, in a particular embodiment of the present invention, STS is used as the major surfactant in the solid sheet. If present, the amount of STS in the solid sheet of the present invention may range from about 10% to about 70%, preferably from about 20% to about 65%, more preferably from about 40% to about 60%, by total weight of the solid sheet.

Another category of anionic surfactants suitable for practice of the present invention include $C_6$-$C_{20}$ linear or branched alkylalkoxy sulfates (AAS). Among this category, linear or branched alkylethoxy sulfates (AES) having the respective formulae $RO(C_2H_4O)_xSO_3M$ are particularly preferred, wherein R is alkyl or alkenyl of from about 6 to about 20 carbon atoms, x is 1 to 10, and M is a water-soluble cation such as ammonium, sodium, potassium and triethanolamine. Preferably, R has from about 6 to about 18, preferably from about 8 to about 16, more preferably from about 10 to about 14, carbon atoms. The AES surfactants are typically made as condensation products of ethylene oxide and monohydric alcohol's having from about 6 to about 20 carbon atoms. Useful alcohols can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized. Highly preferred AES are those comprising a mixture of individual compounds, said mixture having an average alkyl chain length of from about 10 to about 16 carbon atoms and an average degree of ethoxylation of from about 1 to about 4 moles of ethylene oxide. If present, the the amount of AAS in the solid sheet of the present invention may range from about 2% to about 40%, preferably from about 5% to about 30%, more preferably from about 8% to about 12%, by total weight of the solid sheet.

Other suitable anionic surfactants include water-soluble sulphonates of the general formula $[R^1$—$SO_3$-M], wherein $R^1$ is chosen from the group consisting of a straight or branched chain, saturated aliphatic hydrocarbon radical having from about 6 to about 20, preferably about 10 to about 18, carbon atoms; and M is a cation. Preferred are alkali metal and ammonium sulfonated $C_{10-18}$ n-paraffins. Other suitable anionic surfactants include olefin sulfonates having about 12 to about 24 carbon atoms. The α-olefins from which the olefin sulfonates are derived are mono-olefins having about 12 to about 24 carbon atoms, preferably about 14 to about 16 carbon atoms. Preferably, they are straight chain olefins.

Another class of anionic surfactants suitable for use in the fabric and home care compositions is the β-alkyloxy alkane sulfonates. These compounds have the following formula:

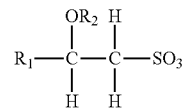

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Still other suitable anionic surfactants are the succinamates, examples of which include disodium N-octadecyl sulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Nonionic surfactants that can be included into the solid sheet of the present invention may be any conventional nonionic surfactants, including but not limited to: alkyl alkoxylated alcohols, alkyl alkoxylated phenols, alkyl polysaccharides (especially alkyl glucosides and alkyl polyglucosides), polyhydroxy fatty acid amides, alkoxylated fatty acid esters, sucrose esters, sorbitan esters and alkoxylated derivatives of sorbitan esters, amine oxides, and the like. Preferred nonionic surfactants are those of the formula $R^1(OC_2H_4)_nOH$, wherein $R^1$ is a $C_8$-$C_{18}$ alkyl group or alkyl phenyl group, and n is from about 1 to about 80. Particularly preferred are $C_8$-$C_{18}$ alkyl ethoxylated alcohols having a weight average degree of ethoxylation from about 1 to about 20, preferably from about 5 to about 15, more preferably from about 7 to about 10, such as NEODOL® nonionic surfactants commercially available from Shell. Other non-limiting examples of nonionic surfactants useful herein include: $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols (BA); $C_{14}$-$C_{22}$ mid-chain branched alkyl alkoxylates, $BAE_x$, wherein x is from 1 to 30; alkyl polysaccharides, specifically alkyl polyglycosides; Polyhydroxy fatty acid amides; and ether capped poly(oxyalkylated) alcohol surfactants. Suitable nonionic surfactants also include those sold under the tradename Lutensol® from BASF.

In a preferred embodiment, the nonionic surfactant is selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

The most preferred nonionic surfactants for practice of the present invention include $C_6$-$C_{20}$ linear or branched alkyl-alkoxylated alcohols (AA) having a weight average degree of alkoxylation ranging from 5 to 15, more preferably $C_{12}$-$C_{14}$ linear ethoxylated alcohols having a weight average degree of alkoxylation ranging from 7 to 9. If present, the amount of AA-type nonionic surfactant(s) in the solid sheet of the present invention may range from about 2% to about 40%, preferably from about 5% to about 30%, more preferably from about 8% to about 12%, by total weight of the solid sheet.

Amphoteric surfactants suitable for use in the solid sheet of the present invention includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids.

One category of amphoteric surfactants particularly suitable for incorporation into solid sheets with personal care applications (e.g., shampoo, facial or body cleanser, and the like) include alkylamphoacetates, such as lauroamphoacetate and cocoamphoacetate. Alkylamphoacetates can be comprised of monoacetates and diacetates. In some types of alkylamphoacetates, diacetates are impurities or unintended reaction products. If present, the amount of alkylamphoacetate(s) in the solid sheet of the present invention may range from about 2% to about 40%, preferably from about 5% to about 30%, more preferably from about 10% to about 20%, by total weight of the solid sheet.

Zwitterionic surfactants suitable include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

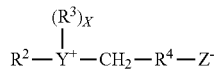

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical, wherein R is a $C_{11}$-$C_{17}$ alkyl, is attached to the nitrogen atom of the betaine are also useful in this invention.

Cationic surfactants can also be utilized in the present invention, especially in fabric softener and hair conditioner products. When used in making products that contain cationic surfactants as the major surfactants, it is preferred that such cationic surfactants are present in an amount ranging from about 2% to about 30%, preferably from about 3% to about 20%, more preferably from about 5% to about 15% by total weight of the solid sheet.

Cationic surfactants may include DEQA compounds, which encompass a description of diamido actives as well as actives with mixed amido and ester linkages. Preferred DEQA compounds are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids.

Other suitable actives for use as a cationic surfactant include reaction products of fatty acids with dialkylenetriamines in, e.g., a molecular ratio of about 2:1, said reaction products containing compounds of the formula:

wherein $R^1$, $R^2$ are defined as above, and each $R^3$ is a $C_{1-6}$ alkylene group, preferably an ethylene group. Examples of these actives are reaction products of tallow acid, canola acid, or oleic acids with diethylenetriamine in a molecular ratio of about 2:1, said reaction product mixture containing N,N"-ditallowoyldiethylenetriamine, N,N"-dicanola-oyldiethylenetriamine, or N,N"-dioleoyldiethylenetriamine, respectively, with the formula:

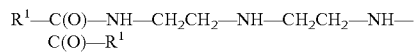

wherein $R^2$ and $R^3$ are divalent ethylene groups, $R^1$ is defined above and an acceptable examples of this structure when $R^1$ is the oleoyl group of a commercially available oleic acid derived from a vegetable or animal source, include EMERSOL® 223LL or EMERSOL® 7021, available from Henkel Corporation.

Another active for use as a cationic surfactant has the formula:

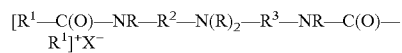

wherein R, $R^1$, $R^2$, $R^3$ and $X^-$ are defined as above. Examples of this active are the di-fatty amidoamines based softener having the formula:

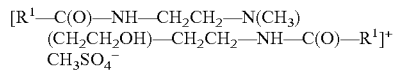

wherein $R^1$—C(O) is an oleoyl group, soft tallow group, or a hardened tallow group available commercially from Degussa under the trade names VARISOFT® 222LT, VARISOFT® 222, and VARISOFT® 110, respectively.

A second type of DEQA ("DEQA (2)") compound suitable as a active for use as a cationic surfactant has the general formula:

wherein each Y, R, $R^1$, and $X^-$ have the same meanings as before. An example of a preferred DEQA (2) is the "propyl" ester quaternary ammonium fabric softener active having the formula 1,2-di(acyloxy)-3-trim ethylammoniopropane chloride.

Suitable polymeric surfactants for use in the personal care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

3. Plasticizers

In a preferred embodiment of the present invention, the flexible, porous, dissolvable solid sheet of the present invention further comprises a plasticizer, preferably in the amount ranging from about 0.1% to about 25%, preferably from about 0.5% to about 20%, more preferably from about 1% to about 15%, most preferably from 2% to 12%, by total weight of said solid sheet. Correspondingly, the wet pre-mixture used for forming such solid sheet may comprise from about 0.02% to about 20% by weight of said wet pre-mixture, in one embodiment from about 0.1% to about 10% by weight of said wet pre-mixture, in one embodiment from about 0.5% to about 5% by weight of the wet pre-mixture.

Suitable plasticizers for use in the present invention include, for example, polyols, copolyols, polycarboxylic acids, polyesters, dimethicone copolyols, and the like.

Examples of useful polyols include, but are not limited to: glycerin, diglycerin, ethylene glycol, polyethylene glycol (especially 200-600), propylene glycol, butylene glycol, pentylene glycol, glycerol derivatives (such as propoxylated glycerol), glycidol, cyclohexane dimethanol, hexanediol, 2,2,4-trimethylpentane-1,3-diol, pentaerythritol, urea, sugar alcohols (such as sorbitol, mannitol, lactitol, xylitol, maltitol, and other mono- and polyhydric alcohols), mono-, di- and oligo-saccharides (such as fructose, glucose, sucrose, maltose, lactose, high fructose corn syrup solids, and dextrins), ascorbic acid, sorbates, ethylene bisformamide, amino acids, and the like.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

Particularly preferred examples of plasticizers include glycerin, ethylene glycol, polyethylene glycol, propylene glycol, and mixtures thereof. Most preferred plasticizer is glycerin.

4. Additional Ingredients

In addition to the above-described ingredients, e.g., the water-soluble polymer, the surfactant(s) and the plasticizer, the solid sheet of the present invention may comprise one or more additional ingredients, depending on its intended application. Such one or more additional ingredients may be selected from the group consisting of fabric care actives, dishwashing actives, hard surface cleaning actives, beauty and/or skin care actives, personal cleansing actives, hair care actives, oral care actives, feminine care actives, baby care actives, and any combinations thereof.

Suitable fabric care actives include but are not limited to: organic solvents (linear or branched lower $C_1$-$C_8$ alcohols, diols, glycerols or glycols; lower amine solvents such as $C_1$-$C_4$ alkanolamines, and mixtures thereof; more specifically 1,2-propanediol, ethanol, glycerol, monoethanolamine and triethanolamine), carriers, hydrotropes, builders, chelants, dispersants, enzymes and enzyme stabilizers, catalytic materials, bleaches (including photobleaches) and bleach activators, perfumes (including encapsulated perfumes or perfume microcapsules), colorants (such as pigments and dyes, including hueing dyes), brighteners, dye transfer inhibiting agents, clay soil removal/anti-redeposition agents, structurants, rheology modifiers, suds suppressors, processing aids, fabric softeners, anti-microbial agents, and the like.

Suitable hair care actives include but are not limited to: moisture control materials of class II for frizz reduction (salicylic acids and derivatives, organic alcohols, and esters), cationic surfactants (especially the water-insoluble type having a solubility in water at 25° C. of preferably below 0.5 g/100 g of water, more preferably below 0.3 g/100 g of water), high melting point fatty compounds (e.g., fatty alcohols, fatty acids, and mixtures thereof with a melting point of 25° C. or higher, preferably 40° C. or higher, more preferably 45° C. or higher, still more preferably 50° C. or higher), silicone compounds, conditioning agents (such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients), preservatives (such as benzyl alcohol, methyl paraben, propyl paraben and imidazolidinyl urea), pH adjusting agents (such as citric acid, sodium citrate, succinic acid, phosphoric acid, sodium hydroxide, sodium carbonate), salts (such as potassium acetate and sodium chloride), coloring agents, perfumes or fragrances, sequestering agents (such as disodium ethylenediamine tetra-acetate), ultraviolet and infrared screening and absorbing agents (such as octyl salicylate), hair bleaching agents, hair perming agents, hair fixatives, anti-dandruff agents, anti-microbial agents, hair growth or restorer agents, co-solvents or other additional solvents, and the like.

Suitable beauty and/or skin care actives include those materials approved for use in cosmetics and that are described in reference books such as the CTFA Cosmetic Ingredient Handbook, Second Edition, The Cosmetic, Toiletries, and Fragrance Association, Inc. 1988, 1992. Further non-limiting examples of suitable beauty and/or skin care actives include preservatives, perfumes or fragrances, coloring agents or dyes, thickeners, moisturizers, emollients, pharmaceutical actives, vitamins or nutrients, sunscreens, deodorants, sensates, plant extracts, nutrients, astringents, cosmetic particles, absorbent particles, fibers, anti-inflammatory agents, skin lightening agents, skin tone agent (which functions to improve the overall skin tone, and may include vitamin B3 compounds, sugar amines, hexamidine compounds, salicylic acid, 1,3-dihydroxy-4-alkybenzene such as hexylresorcinol and retinoids), skin tanning agents, exfoliating agents, humectants, enzymes, antioxidants, free radical scavengers, anti-wrinkle actives, anti-acne agents, acids, bases, minerals, suspending agents, pH modifiers, pigment particles, anti-microbial agents, insect repellents, shaving lotion agents, co-solvents or other additional solvents, and the like.

The solid sheet of the present invention may further comprise other optional ingredients that are known for use or otherwise useful in compositions, provided that such optional materials are compatible with the selected essential materials described herein, or do not otherwise unduly impair product performance.

Non-limiting examples of product type embodiments that can be formed by the solid sheet of the present invention include laundry detergent products, fabric softening products, hand cleansing products, hair shampoo or other hair treatment products, body cleansing products, shaving preparation products, dish cleaning products, personal care substrates containing pharmaceutical or other skin care actives, moisturizing products, sunscreen products, beauty or skin care products, deodorizing products, oral care products, feminine cleansing products, baby care products, fragrance-containing products, and so forth.

VI. Assembling of Multiple Sheets into Multilayer Dissolvable Solid Articles

Once the flexible, dissolvable, porous solid sheets as described hereinabove are formed, as described hereinabove, two or more of such sheets can be further assembled together to form multilayer dissolvable solid articles of the present invention. The sheets can be combined and/or treated by any means known in the art, examples of which include but are not limited to, chemical means, mechanical means, and combinations thereof. Such combination and/or treatment steps are hereby collectively referred to as a "conversion" process, i.e., which functions to convert two or more flexible, dissolvable, porous sheets of the present invention into a multilayer dissolvable solid article with a desired three-dimensional shape.

It has been a surprising and unexpected discovery of the present invention that the flexible, dissolvable, porous solid sheet articles of the present invention have self-adhering properties, i.e., they can adhere to each other without any added adhesives. Therefore, the conversion process of the present invention does not involve the use or application of any adhesives. For example, it is possible to simply stack two or more of such self-adhering sheets on top of one another and then carry out a simple cut-sealing step to provide a sufficiently strong bonding force between adjacent sheets in said stack. Preferably, the cut-sealing is conducted by using by using a Huasen HAS/B-200 2 tonne or HSC/S-500 50 tonne hydraulic press (commercially available from Yancheng City Huasen Machinery Co., Ltd in Jiangsu Province, China) at a cut angle ranging from about 20° to about 50°. More preferably, the cut-sealing step may be combined with some pressure to further improve bonding between adjacent sheets in the stack.

Further, it has been discovered that slightly increasing the moisture contents of the sheets (e.g., from the original level of 3%-6% to from about 6% to about 12%, preferably from 7% to 11%) shortly before the conversion process can not only increase flexibility of the sheets to avoid potential structural damage to the sheets during the cut-sealing step, but also significantly improve bonding between adjacent sheets in the stack. For example, when the moisture contents of the sheets before conversion are below 6%, noticeable structure damages to the foamed surfaces of the sheets are observed after the cut-sealing step due to the brittleness of the sheets. When the moisture contents of the sheets before conversion are between 6% to 7%, such structural damages are not observed after the conversion, but there are unseal portions along the edges of the stack that are formed by such sheets. More importantly, it has been discovered that subsequent moisture loss from the stack or moisture gain by the stack after the conversion process does not negatively affect the flexibility of the sheets or the bonding between adjacent sheets, i.e., they will remain adhere to each other even if the moisture content drops back to the original level or if the moisture content increases to an even higher level. The moisture contents of the sheets can be readily increased to the level desired for conversion (e.g., from about 6% to about 12%) through a variety of conditioning methods before the conversion process starts. For example, the moisture contents of the solid sheets can be adjusted by storing the solid sheets for about 24 hours in an environment where the air temperature is about 20° C. to about 25° C. with a relative humidity of about 40% to about 50%. Another method of adjusting the moisture contents of the solid sheets is by spraying water directly onto the surfaces of the solid sheets through a pressurized spray system (for example, an Autojet 1550+ from Spraying Systems Co.) with suitable atomization nozzle to ensure a homogeneous coating of water on the solid sheets.

Preferably, the dissolvable solid article is formed by stacking two or more of such flexible, dissolvable, porous sheets in a "head-to-toe" manner, i.e., by ensuring that the bottom surface of a preceding sheet contacts the top surface of a following sheet in the stack. Without being bound by any theory, it is believed that such a "head-to-toe" stacking arrangement provides better overall structural integrity for the multilayer article, versus either a "head-to-head" or "toe-to-toe" stacking arrangement.

In addition to the stacking and cut-sealing steps as described hereinabove, the dissolvable solid article can be further processed by edge-sealing at least a portion of the peripheral of said dissolvable solid article. The edge seal so formed may function to further strengthen the structural integrity and stability of the multilayer structure. The edge-sealing step can be readily conducted by using a Chhong 1 tonne CH217 hydraulic press at a temperature ranging from about 50° C. to about 120° C. and a contact time of from about 0.5 to about 6.0 seconds.

Further, it may be desirable to further improve the dissolution rate of the multilayer dissolvable solid article of the present invention by perforation, to form one or more apertures or holes that extend through all sheets of said dissolvable solid article. Additional embossing or printing steps can also be carried out to further improve the aesthetic appeal of the dissolvable solid article of the present invention.

The multilayer dissolvable solid articles of the present invention may have any desirable three-dimensional shapes, including but not limited to: spherical, cubic, rectangular, polygonal, oblong, cylindrical, rod, sheet, flower-shaped, fan-shaped, star-shaped, disc-shaped, and the like. Preferably, the multilayer dissolvable solid articles of the present invention may be characterized by an Aspect Ratio ranging from 1 to about 10, preferably from about 1.4 to about 9, preferably from about 1.5 to about 8, more preferably from about 2 to about 7, while said Aspect Ratio is the ratio of a maximum dimension D of such solid article over a minimum dimension z that is substantially perpendicular thereto. More preferably, the multilayer dissolvable solid article of the present invention may have a minimal dimension z that is greater than about 3 mm but less than about 20 cm, preferably from about 4 mm to about 10 cm, more preferably from about 5 mm to about 30 mm.

The above-described multilayer dissolvable solid article may comprise more than two of such flexible, dissolvable, porous sheets. For example, it may comprise from about 4 to about 50, preferably from about 5 to about 40, more preferably from about 6 to about 30, of said flexible, dissolvable, porous sheets. The improved OCF structures in the flexible, dissolvable, porous sheets made according to the present invention allow stacking of many sheets (e.g., 15-40) together, while still providing a satisfactory overall dissolution rate for the stack.

In a particularly preferred embodiment of the present invention, the multilayer dissolvable solid article comprises from 15 to 40 layers of the above-described flexible, dissolvable, porous sheets and has an aspect ratio ranging from about 2 to about 7.

The multilayer dissolvable solid article of the present invention may comprise individual sheets of different colors, which are visual from an external surface (e.g., one or more side surfaces) of such article. Such visible sheets of different colors are aesthetically pleasing to the consumers. Further, the different colors of individual sheets may provide visual cues indicative of different benefit agents contained in the individual sheets. For example, the multilayer dissolvable solid article may comprise a first sheet that has a first color and contains a first benefit agent and a second sheet that has a second color and contains a second benefit, while the first color provides a visual cue indicative of the first benefit agent, and while the second color provides a visual cue indicative of the second benefit agent.

Further, one or more functional ingredients (non-adhesives) can be "sandwiched" between individual sheets of the multilayer dissolvable solid article as described hereinabove, e.g., by spraying, sprinkling, dusting, coating, spreading, dipping, injecting, or even vapor deposition. In order to avoid interference of such functional ingredients with the cutting seal or edge seal near the peripherals of the individual sheets, it is preferred that such functional ingredients are located within a central region between two adjacent sheets, which is defined as a region that is spaced apart from the peripherals of such adjacent sheets by a distance that is at least 10% of the maximum Dimension D.

Suitable functional ingredients can be selected from the group consisting of cleaning actives (surfactants, free perfumes, encapsulated perfumes, perfume microcapsules, silicones, softening agents, enzymes, bleaches, colorants, builders, rheology modifiers, pH modifiers, and combinations thereof) and personal care actives (e.g., emollients, humectants, conditioning agents, and combinations thereof).

TEST METHODS

Test 1: Scanning Electron Microscopic (SEM) Method for Determining Surface Average Pore Diameter of the Sheet Article An Hitachi TM3000 Tabletop Microscope (S/N: 123104-04) is used to acquire SEM micrographs of samples. Samples of the solid sheet articles of the present invention are approximately 1 cm×1 cm in area and cut from larger sheets. Images are collected at a magnification of 50×, and the unit is operated at 15 kV. A minimum of 5 micrograph images are collected from randomly chosen locations across each sample, resulting in a total analyzed area of approximately 43.0 $mm^2$ across which the average pore diameter is estimated.

The SEM micrographs are then firstly processed using the image analysis toolbox in Matlab. Where required, the images are converted to grayscale. For a given image, a histogram of the intensity values of every single pixel is generated using the 'imhist' Matlab function. Typically, from such a histogram, two separate distributions are obvious, corresponding to pixels of the brighter sheet surface and pixels of the darker regions within the pores. A threshold value is chosen, corresponding to an intensity value between the peak value of these two distributions. All pixels having an intensity value lower than this threshold value are then set to an intensity value of 0, while pixels having an intensity value higher are set to 1, thus producing a binary black and white image. The binary image is then analyzed using ImageJ (https://imagej.nih.gov, version 1.52a), to examine both the pore area fraction and pore size distribution. The scale bar of each image is used to provide a pixel/mm scaling factor. For the analysis, the automatic thresholding and the analyze particles functions are used to isolate each pore. Output from the analyze function includes the area fraction for the overall image and the pore area and pore perimeter for each individual pore detected.

Average Pore Diameter is defined as $D_A50$: 50% of the total pore area is comprised of pores having equal or smaller hydraulic diameters than the $D_A50$ average diameter.

Hydraulic diameter='4*Pore area $(m^2)$/Pore perimeter $(m)$'.

It is an equivalent diameter calculated to account for the pores not all being circular.

Test 2: Micro-Computed Tomographic (μCT) Method for Determining Overall or Regional Average Pore Size and Average Cell Wall Thickness of the Open Cell Foams (OCF)

Porosity is the ratio between void-space to the total space occupied by the OCF. Porosity can be calculated from μCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a μCT X-ray scanning instrument capable of acquiring a dataset at high isotropic spatial resolution. One example of suitable instrumentation is the SCANCO system model 50 μCT scanner (Scanco Medical AG, Brüttisellen, Switzerland) operated with the following settings: energy level of 45 kVp at 133 μA; 3000 projections; 15 mm field of view; 750 ms integration time; an averaging of 5; and a voxel size of 3 μm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning. Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from Thermo Fisher Scientific and MATLAB (R2017a) from Mathworks.

Test 3: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet article of the present invention is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

$$\text{Open cell percentage} = \text{Open cell volume of sample}/\text{Geometric volume of sample} * 100$$

It is recommended that these measurements be conducted by Micromeritics Analytical Services, Inc. (One Micromeritics Dr, Suite 200, Norcross, GA 30093). More information on this technique is available on the Micromeritics Analytical Services web sites (www.particletesting.com or www.micromeritics.com), or published in "Analytical Methods in Fine particle Technology" by Clyde Orr and Paul Webb.

Test 4: Final Moisture Content of the Sheet Article

Final moisture content of the solid sheet article of the present invention is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

Test 5: Thickness of the Sheet Article

Thickness of the flexible, porous, dissolvable solid sheet article of the present invention is obtained by using a micrometer or thickness gage, such as the Mitutoyo Corporation Digital Disk Stand Micrometer Model Number IDS-1012E (Mitutoyo Corporation, 965 Corporate Blvd, Aurora, IL, USA 60504). The micrometer has a 1-inch diameter platen weighing about 32 grams, which measures thickness at an application pressure of about 0.09 psi (6.32 gm/cm$^2$).

The thickness of the flexible, porous, dissolvable solid sheet article is measured by raising the platen, placing a section of the sheet article on the stand beneath the platen, carefully lowering the platen to contact the sheet article, releasing the platen, and measuring the thickness of the sheet article in millimeters on the digital readout. The sheet article should be fully extended to all edges of the platen to make sure thickness is measured at the lowest possible surface pressure, except for the case of more rigid substrates which are not flat.

Test 6: Basis Weight of the Sheet Article

Basis Weight of the flexible, porous, dissolvable solid sheet article of the present invention is calculated as the weight of the sheet article per area thereof (grams/m$^2$). The area is calculated as the projected area onto a flat surface perpendicular to the outer edges of the sheet article. The solid sheet articles of the present invention are cut into sample squares of 10 cm×10 cm, so the area is known. Each of such sample squares is then weighed, and the resulting weight is then divided by the known area of 100 cm$^2$ to determine the corresponding basis weight.

For an article of an irregular shape, if it is a flat object, the area is thus computed based on the area enclosed within the outer perimeter of such object. For a spherical object, the area is thus computed based on the average diameter as 3.14×(diameter/2)$^2$. For a cylindrical object, the area is thus computed based on the average diameter and average length as diameter×length. For an irregularly shaped three-dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

Test 7: Density of the Sheet Article

Density of the flexible, porous, dissolvable solid sheet article of the present invention is determined by the equation: Calculated Density=Basis Weight of porous solid/(Porous Solid Thickness×1,000). The Basis Weight and Thickness of the dissolvable porous solid are determined in accordance with the methodologies described hereinabove.

Test 8: Specific Surface Area of the Sheet Article

The Specific Surface Area of the flexible, porous, dissolvable solid sheet article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, GA 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

Test 9: Dissolution Rate

The dissolution rate of dissolvable sheets or solid articles of the present invention is measured as follows:
1. 400 ml of deionized water at room temperature (25° C.) is added to a 1 L beaker, and the beaker is then placed on a magnetic stirrer plate.
2. A magnetic stirrer bar having length 23 mm and thickness of 10 mm is placed in the water and set to rotate at 300 rpm.
3. A Mettler Toledo S230 conductivity meter is calibrated to 1413 µS/cm and the probe placed in the beaker of water.
4. For each experiment, the number of samples is chosen such that a minimum of 0.2 g of sample is dissolved in the water.
5. The data recording function on the conductivity meter is started and the samples are dropped into the beaker. For 5 seconds a flat steel plate with diameter similar to that of the glass beaker is used to submerge the samples below the surface of the water and prevent them from floating to the surface.
6. The conductivity is recorded for at least 10 minutes, until a steady state value is reached.
7. In order to calculate the time required to reach 95% dissolution, a 10 second moving average is firstly calculated from the conductivity data. The time at which this moving average surpassed 95% of the final steady state conductivity value is then estimated and taken as the time required to achieve 95% dissolution.

Test 10: Normalized Crystallinity of the Sheet Article

Normalized Crystallinity of the flexible, porous, dissolvable sheets of the present invention can be measured by the following steps.

First, the PVA polymer used for forming the flexible, porous, dissolve sheet of interest is dissolved in a sufficient amount of water at 85° C. and mixed for about 1 hour, followed by adding all the other ingredients used for forming such sheet and continuing to mix for another hour at 85° C., so as to form a wet pre-mixture with a solid content of from about 25% to about 35%. The resulting wet premixture is then allowed to cool down to room temperature for storage and further testing.

Alternatively, the flexible, porous, dissolve sheet of interest itself can be dissolved or dispersed in a sufficient amount of water at similar conditions to form such a wet pre-mixture. For example, a predetermined amount (e.g., 20 g or more) of the dried sheet is weighed and obtained, followed by measuring its moisture content (following the same procedure as described in Test 4). The moisture content information is then used to calculate the amount of water required to dissolve the predetermined amount of dried sheet to form a wet pre-mixture having a solid content of from about 25% to about 35%. Next, the calculated amount of water is heated up in a beaker to about 85° C., and the predetermined amount of dried sheet is then slowly added in 1 g pieces with overhead stirring. The heating and stirring continue for at least 1 hour until there are no visible solid residues of the sheet, so as to form the desired wet pre-mixture, which is then cooled down to room temperature for storage and further testing.

Next, the wet pre-mixture is poured into a sample holder of about 19 mm×19 mm×5 mm and dried at 15° C. and 20% Relative Humidity for about 24 hours, to form a dry test sheet. Such a dry test sheet contains little or no pores (due to the lack of any aeration step) and is particularly suitable for the subsequent crystallinity measurement.

X-ray diffraction (XRD) is used in the present invention to measure crystallinity of the above-mentioned dry test sheet, and the crystallinity parameter so measured is deemed as the Normalized Crystallinity of the flexible, porous, dissolvable sheet (from which, or based on which, the dry test sheet has been made).

Specifically, X-ray diffraction data is first obtained by using a Rigaku Ultima IV X-ray diffractometer (commercially available from Rigaku Americas Corporation located in Texas, USA) under Ni-filtered CuKα radiation ($\lambda$=1.54060 Å) generated at a voltage of 40 kV and a current of 40 mA. A scan speed of 10 degree/min from the 2θ range of 4° to 60° is used to take the diffraction patterns. The equipment settings applied include: Div Slit ½ degree; DivH.L. Slit 10 mm; Sct Slit 8 mm; and Rec Slit 'Open'.

Subsequently, MDI Jade Version 2010 software (commercially available from Materials Data, Inc. located in California, USA) is employed to process the XRD patterns by separate the background and the overlapped peaks. After separation of the X-ray diffraction lines, crystallinity of the dry test sheet is calculated based on the respective areas under the crystalline peaks and those under the amorphous curve.

Following is a detailed, step-by-step description of the XRD pattern analysis and crystallinity calculation methodology:

Load the XRD spectrum into MDI Jade software;

Zoom in the area from 10° to 40° degree in the spectrum by dragging a zoom window;

Select an approximate region for each peak to separate the background and the overlapped peaks;

Select a fitting model. For example:
1) Pearson-VII can be applied;
2) Select K-alpha2 Present and Skewness=0 as the profile parameters;
3) Select Initial Width as FWHM (Full Width at Half Maximum) Curve without specify and Initial Location as Peak Search;

Refine the spectrum and review residue value (lower means better fit), e.g., r<3% is deemed as a good fitting quality;

Identify the amorphous phase, the crystalline phase and background in the XRD spectrum according to the FWHM values, e.g., FWHM<1 is the crystalline phase, 1<FWHM<10 is the amorphous phase, and FWHM>10 is background;

Calculate the crystallinity index (CI) as $x\% = \frac{\text{Crystalline Area}}{\text{Crystalline Area} + \text{Amorphous Area}} \times 100\%$.

For example, when a dry test sheet has a XRD pattern having three (3) crystalline peaks with respective area percentages (%) of 9.9, 6.3 and 0.3, and a total amorphous area percentage (%) of 35.5, its CI is calculated as $$x\% = \frac{(9.9 + 6.6 + 0.3)}{(9.9 + 6.6 + 0.3 + 35.5)} \times 100\% = 32\%.$$

Test 11: Adhesion Score and Adhesion Stability Score for Adjacent Sheets in the Dissolvable Solid Article To measure the adhesion force between any two adjacent sheets in a multilayer solid article according to the present invention, such adjacent sheets are first separated from each other and then conditioned by placing them in a temperature and humidity-controlled room at a temperature of about 23-24.5° C. and a relative humidity (RH) of about 41-45% for about 1 hour. During the conditioning process, the sheets are laid out individually, e.g., on a flat surface, and are not stacked upon one another.

The adjacent sheets so separated and conditioned are then stacked upon one another in a head-to-toe configuration. Care is taken not to apply excessive pressure to the sheet stack during the entirety of testing, where excessive pressure is defined as any applied pressure that is sufficient to result in a thickness change of 0.05 mm or greater in either of the two adjacent sheets.

At least twelve (12) test samples of about 2 cm×2 cm are subsequently cut out from the larger sheet stack by using a paper guillotine. All four edges of each 2 cm×2 cm test sample are cut by the paper guillotine. None of the existing edges of the larger sheet stack is used as the edges of the smaller 2 cm×2 cm test samples. The mass of each test sample after cutting is recorded, while the recorded mass of all test samples is about 0.22 g with a standard deviation of about 0.03 g.

The edges of each test sample are then thoroughly examined by naked eye so as to identify areas of obvious separation between the adjacent sheets in such test sample, and the exact length of each edge separation is measured by using a ruler. The edge adhesion percentage (x %) is then calculated as $$x\% = \frac{(8 \text{ cm} - \text{Total Length of Edge Separation})}{8 \text{ cm}} \times 100\%.$$

An "Edge Adhesion Score' ranging from 0 to 3 is then assigned to each 2 cm×2 cm test sample based on the edge adhesion percentage so calculated, according to the following criteria:

0—if the edge adhesion percentage (x %) is <5%, i.e., less than 5% of the edges of the two adjacent sheets in the test sample are adhered to one another;

1—if the edge adhesion percentage (x %) is <5% but <25%, i.e., exactly 5% or between 5 to 25% of the edges of the two adjacent sheets in the test sample are adhered to one another;

2—if the edge adhesion percentage (x %) is <25% but <95%, i.e., exactly 25% or between 25% to 95% of the edges of the two adjacent sheets in the test sample are adhered to one another;

3—if the edge adhesion percentage (x %) is <95%, i.e., exactly or greater than 95% of the edges of the two adjacent sheets in the test sample are adhered to another.

The Adhesion Score (AdS) of the two adjacent sheets tested is then calculated as the average of the Edge Adhesion Scores of the 12 test samples cut out from the same larger sheet stack, which is formed by stacking the two adjacent sheets one upon another after they have been separated and conditioned as described hereinabove.

Further, each of the 12 test samples is subject to a drop test after its Edge Adhesion Score has been calculated. Specifically, a pair of plastic thumb forceps are used to place the respective test sample at a drop location that is about 1 meter above a solid, flat surface (e.g., the floor or a tabletop). The test sample is oriented so that at least one of its four edge surfaces formed by the cutting process as mentioned hereinabove is parallel to the solid, flat surface (while the test sample itself is substantially perpendicular to the solid, flat surface), and it is then released from the drop location. In this manner, the test sample will first land on said edge surface that is parallel to the solid, flat surface. The edges of each test sample after such a drop test are then thoroughly examined again, and a new Edge Adhesion Score is calculated accordingly.

The Adhesion Stability Score (AdSS) of the two adjacent sheets tested is calculated as the average of the new Edge Adhesion Scores of the 12 test samples after they have undergone the drop test.

EXAMPLES

Example 1

Different OCF Structures in Solid Sheets Made by Different Heating/Drying Arrangements A wet pre-mixture with the following surfactant/polymer composition for laundry care as described in Table 1 below is prepared.

TABLE 1

(LAUNDRY CARE FORMULATION)

| Materials: | (Wet) w/w % | (Dry) w/w % |
|---|---|---|
| Polyvinyl alcohol (with a degree of polymerization of about 1700) | 7.58 | 21 |
| Glycerin | 1.08 | 3 |
| Linear Alkylbenzene Sulfonate | 19.12 | 53 |
| Sodium Laureth-3 Sulfate | 3.61 | 10 |
| C12-C14 Ethoxylated alcohol | 3.61 | 10 |
| Water | Balance | Balance |

Viscosity of the wet pre-mixture composition as described in Table 1 is about 14309.8 cps. After aeration, the average density of such aerated wet pre-mixture is about 0.25 g/cm$^3$.

Inventive flexible, porous, dissolvable solid sheet A is prepared from the above wet pre-mixture as described in Table 1 sing a continuous aerator (Aeros) and a rotary drum drier, with the following settings and conditions as described in Table 2 below:

TABLE 2

(DRUM DRYING)

| Parameters | Value |
|---|---|
| Wet pre-mixture temperature before and during aeration | 80° C. |
| Aeros feed pump speed setting | 600 |
| Aeros mixing head speed setting | 500 |
| Aeros air flow rate setting | 100 |
| Wet pre-mixture temperature before drying | 60° C. |
| Rotary drum drier surface temperature | 130° C. |
| Rotary drum drier rotational speed | 0.160 rpm |
| Drying time | 4.52 min |

Further, a comparative flexible, porous, dissolvable solid sheet I is prepared from the above wet pre-mixture as described in Table 1 using a continuous aerator (Oakes) and a mold placed on an impingement oven, with the following settings and conditions as described in Table 3 below:

TABLE 3

(IMPINGEMENT OVEN DRYING)

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Impingement oven temperature | 130° C. |
| Drying time | 6 min |

Tables 4-7 as follows summarize various physical parameters and pore structures measured for the inventive solid sheet A and comparative solid sheet I made from the above-described wet pre-mixtures and drying processes.

TABLE 4

(PHYSICAL PARAMETERS)

| Samples | Formulation | Drying Process | Average Basis Weight g/m$^2$ | Average Density g/cm$^3$ | Average Thickness mm | Specific Surface Area m$^2$/g |
|---|---|---|---|---|---|---|
| A | Laundry Care | Rotary Drum | 147.5 | 0.118 | 1.265 | 0.115 |
| Comp I | Laundry | Impingement Oven | 116.83 | 0.118 | 1.002 | — |

TABLE 5

(OVERALL PORE STRUCTURES)

| Samples | Formulation | Drying Process | Percent Open Cell Content % | Overall Average Pore Size μm | Average Cell Wall Thickness μm |
|---|---|---|---|---|---|
| A | Laundry Care | Rotary Drum | 90.75 | 467.1 | 54.3 |
| Comp I | Laundry Care | Impingement Oven | — | 197.6 | 15.2 |

TABLE 6

(SURFACE AND REGIONAL PORE STRUCTURES)

| Samples | Formulation | Drying Process | Surface Average Pore Diameter (μm) Top | Average Pore Size (μm) Top | Middle | Bottom |
|---|---|---|---|---|---|---|
| A | Laundry Care | Rotary Drum | 201.5 | 458.3 | 479.1 | 463.9 |
| Comp I | Laundry Care | Impingement Oven | 53.3 | 139.9 | 213.1 | 238.7 |

TABLE 7

(VARIATIONS BETWEEN REGIONAL PORE STRUCTURES)

| Samples | Formulation | Drying Process | Cross-Region Relative STD (%) | Btw-Region Ratios of Average Pore Sizes Bottom-to-Top | Bottom-to-Middle | Middle-to-Top |
|---|---|---|---|---|---|---|
| A | Laundry Care | Rotary Drum | 2.31% | 1.012 | 0.968 | 1.046 |
| Comp I | Laundry Care | Impingement Oven | 25.99% | 1.706 | 1.120 | 1.523 |

Figure 7A:
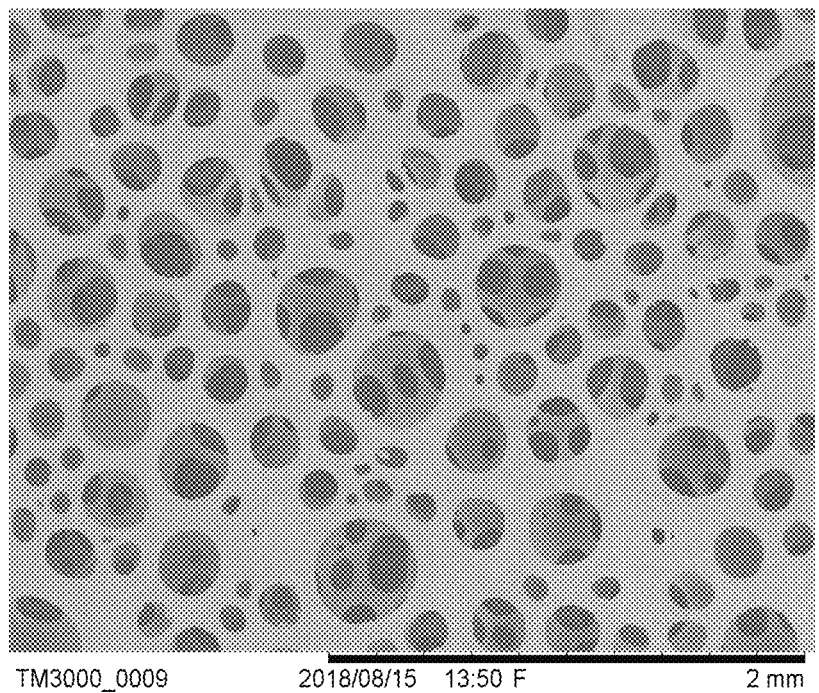
FIG. 7A shows a Scanning Electron Microscopic (SEM) image of the top surface of an inventive flexible, porous, dissolvable sheet containing fabric care actives, which is made by a process employing a rotary drum-based heating/drying arrangement.
Figure 7B:
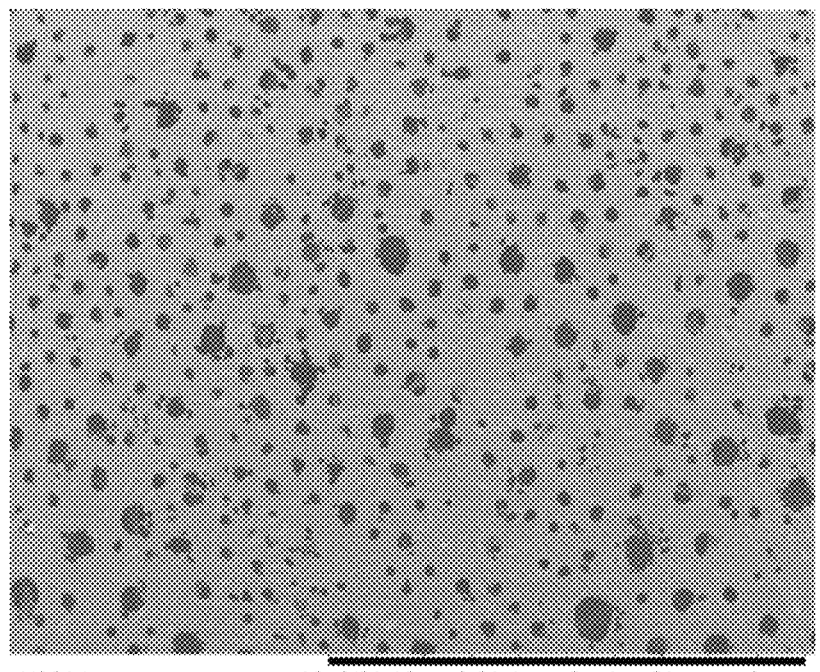
FIG. 7B shows a SEM image of the top surface of a comparative flexible, porous, dissolvable sheet containing the same fabric care actives as the sheet shown in FIG. 7A, but which is made by a process employing an impingement oven-based heating/drying arrangement.

The above data demonstrates that the inventive solid sheet A made according to a method of the present invention have Top Surface Average Pore Diameters of greater than 100 μm, while the comparative solid sheet I does not. Specifically, FIG. 7A shows a Scanning Electron Microscopic (SEM) image of the top surface of the inventive sheet A, while FIG. 7B shows a SEM image of the top surface of the comparative solid sheet Comp I. Further, the above data demonstrates that the inventive solid sheet A has significantly less regional variations in its Average Pore Sizes than the comparative solid sheet I, especially with significantly smaller ratios of the bottom Average Pore Size over the top Average Pore Size.

Example 2

Comparative Adhesion Scores and Adhesion Stability Scores of Multilayer Dissolvable Solid Articles Formed by Sheets of Different Normalized Crystallinity Values Wet pre-mixtures with the following surfactant/polymer compositions 1-5 as described in Tables 8 to 12 below are prepared:

TABLE 8

(1—PERSONAL CARE FORMULATION)

| Chemical | (Wet) w/w % | (Dry) w/w % |
|---|---|---|
| Polyvinyl alcohol (Degree of polymerization 1700) | 8.1 | 23.5 |
| Glycerin | 3.2 | 9.4 |
| Sodium Laureth-3 Sulfate | 1.5 | 4.4 |
| Sodium Laureth-1 Sulfate | 13.3 | 38.5 |
| Sodium Lauroamphoacetate | 5.9 | 17.1 |
| Guar Hydroxypropyltrimonium Chloride | 0.4 | 1.2 |
| Citric acid (anhydrous) | 1.0 | 2.9 |
| Water | Balance | Balance |

TABLE 9

(2—PERSONAL CARE FORMULATION)

| Chemical | (Wet) w/w % | (Dry) w/w % |
|---|---|---|
| Polyvinyl alcohol (Degree of polymerization 1700) | 8.5 | 24.5 |
| Glycerin | 3.2 | 9.3 |
| Sodium Lauryl Sulfate (unethoxylated) | 13.1 | 37.7 |
| Sodium Laureth-3 Sulfate | 3.6 | 10.2 |
| Sodium Lauroamphoacetate | 4.0 | 11.5 |
| Guar Hydroxypropyltrimonium Chloride | 0.4 | 1.2 |
| Citric acid (anhydrous) | 0.7 | 2.1 |
| Sodium Benzoate | 0.2 | 0.5 |
| Water | Balance | Balance |

TABLE 10

(3—LAUNDRY CARE FORMULATION)

| Chemical | (Wet) w/w % | (Dry) w/w % |
|---|---|---|
| Polyvinyl alcohol (Degree of polymerization 1700) | 7.6 | 21.0 |
| Glycerin | 1.1 | 3.0 |
| Linear Alkylbenzene Sulfonate | 19.1 | 52.9 |
| Sodium Laureth-3 Sulfate | 3.6 | 10.0 |
| C12-C14 Ethoxylated alcohol | 3.6 | 10.0 |
| Water | Balance | Balance |

TABLE 11

(4—LAUNDRY CARE FORMULATION)

| Chemical | (Wet) w/w % | (Dry) w/w % |
|---|---|---|
| Polyvinyl alcohol (Degree of polymerization 1700) | 3.1 | 6.9 |
| Polyvinyl alcohol (Degree of polymerization 500) | 6.2 | 13.9 |
| Glycerin | 3.1 | 6.9 |

TABLE 11-continued (4—LAUNDRY CARE FORMULATION)

| Chemical | (Wet) w/w % | (Dry) w/w % |
|---|---|---|
| Sodium Lauryl Sulfate (Unethoxylated) | 17.4 | 39.3 |
| Sodium C14-C16 alpha olefin sulfonate | 13.3 | 30.0 |
| Water | Balance | Balance |

TABLE 12

(5—FABRIC ENHANCER FORMULA)

| Chemical | (Wet) w/w % | (Dry) w/w % |
|---|---|---|
| Polyvinyl alcohol (Degree of polymerization 1700) | 7.2 | 20.0 |
| Glycerin | 7.2 | 20.0 |
| C12-C14 Ethoxylated alcohol | 9.1 | 25.1 |
| Citric acid (anhydrous) | 1.5 | 4.1 |
| Ethanaminium, 2-hydroxy-N-(2-hydroxyethyl)-N,N-dimethyl-, esters with C16-18 and C18-unsatd. fatty acids, chlorides | 9.0 | 25.0 |
| 2-Propanol | 1.0 | 2.8 |
| Water | Balance | Balance |

Flexible, porous, dissolvable solid sheets are prepared from the above wet pre-mixtures 1-5 as described in Tables 8 to 12 using a continuous aerator (Aeros) and a rotary drum drier, with the following settings and conditions as described in Table 13 below:

TABLE 13

(DRUM DRYING)

| Parameters | Value |
|---|---|
| Wet pre-mixture temperature before and during aeration | 80° C. |
| Aeros feed pump speed setting | 600 |
| Aeros mixing head speed setting | 500 |
| Aeros air flow rate setting | 100 |
| Wet pre-mixture temperature before drying | 60° C. |
| Rotary drum drier surface temperature | 130° C. |
| Rotary drum drier rotational speed | 0.118 rpm |
| Drying time | 6.81 min |

Respective Normalized Crystallinity values of the above-described wet pre-mixtures 1-5 are measured according to Test Method 10 hereinabove. Further, respective Adhesion Score (AdS) and Adhesion Stability Score (AdSS) of the flexible, porous, dissolvable solid sheets prepared from said wet pre-mixtures 1-5 (i.e., AdS and AdSS between two adjacent sheets formed by the same wet pre-mixture and the same drying process) are measured according to Test Method 11. Following Table 14 lists the measurement results:

TABLE 13

| FORMULATION | Normalized Crystallinity (%) | AdS | AdSS |
|---|---|---|---|
| 1—PERSONAL CARE FORMULATION | 2.80 | 2.75 | 2.75 |
| 2—PERSONAL CARE FORMULATION | 23.00 | 0.58 | 0.17 |
| 3—LAUNDRY CARE FORMULATION | 0.00 | 2.67 | 2.80 |
| 4—LAUNDRY CARE FORMULATION | 32.00 | 0.00 | 0.08 |
| 5—FABRIC ENHANCER FORMULA | 3.00 | 2.83 | 3.00 |

It is observed that the flexible, porous, dissolvable solid sheets 2 and 4 have significantly higher Normalized Crystallinity values, in comparison with sheets 1, 3, and 5. Further, sheets 2 and 4, which contain significant amounts of unethoxylated alkyl sulfates (AS) significantly lower AdS and AdSS, while sheets 1, 3, and 5 that are substantively AS-free are characterized by significantly higher AdS and AdSS.

Example 3

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid article comprising two or more flexible, dissolvable, porous sheets, wherein each of said two or more sheets comprises a water-soluble polymer and a surfactant and is characterized by a Percent Open Cell Content of from 80% to 100% and an Overall Average Pore Size of from 100 μm to 2000 μm; and wherein at least two adjacent sheets in said article are characterized by an Adhesion Score (AdS) of no less than 1, but the contacting surfaces of said at least two adjacent sheets are free of adhesives, wherein each of said two or more flexible, dissolvable, porous sheets is characterized by a Normalized Crystallinity of not more than 15% and the article is free of unalkoxylated $C_6$-$C_{20}$ linear or branched alkyl sulfates.

2. The dissolvable solid article of claim 1, wherein the Adhesion Score (AdS) of said two adjacent sheets in said article is from 1 to 3.

3. The dissolvable solid article of claim 1, wherein said two adjacent sheets in said article is further characterized by an Adhesion Stability Score (AdSS) of no less than 0.5.

4. The dissolvable solid article according to claim 1, wherein each of said two or more flexible, dissolvable, porous sheets is characterized by a Normalized Crystallinity of not more than 5%.

5. The dissolvable solid article according to claim 1, wherein each of said two or more flexible, dissolvable, porous sheets has opposing top and bottom surfaces, said top surface having a Surface Average Pore Diameter that is greater than 120 μm.

6. The dissolvable solid article of claim 5, wherein each of said two or more flexible, dissolvable, porous sheets comprises a top region adjacent to said top surface, a bottom region adjacent to said bottom surface, and a middle region therebetween; and wherein said top, middle, and bottom regions have the same thickness, and each of said top, middle and bottom regions is characterized by an Average Pore Size; and wherein the ratio of Average Pore Size in said bottom region over that in said top region is from 0.6 to 1.5.

7. The dissolvable solid article of claim 5, wherein said two or more flexible, dissolvable, porous sheets are arranged in said dissolvable solid article so that the bottom surface of a preceding sheet contacts the top surface of a following sheet.

8. The dissolvable solid article according to claim 1, wherein at least one of said two or more flexible, dissolvable, porous sheets comprises from 15% to 30% of said water-soluble polymer by total weight of said sheet; and wherein said water-soluble polymer has a weight average molecular weight of from 50,000 to 400,000 Daltons; and wherein said water-soluble polymer is a polyvinyl alcohol characterized by a degree of hydrolysis ranging from 70% to 90%.

9. The dissolvable solid article according to claim 1, wherein at least one of said two or more flexible, dissolvable, porous sheets comprises 40% to 80%, of said surfactant by total weight of said sheet.

10. The dissolvable solid article according to claim 1, wherein at least one of said two or more flexible, dissolvable, porous sheets comprises from 1% to 15%, of a plasticizer by total weight of said sheet; and wherein said plasticizer is selected from the group consisting of glycerin, ethylene glycol, polyethylene glycol, propylene glycol, and combinations thereof.

11. The dissolvable solid article according to claim 1, wherein each of said two or more flexible, dissolvable, porous sheets is characterized by:
   a Percent Open Cell Content of from 90% to 100%; and/or
   an Overall Average Pore Size of from 200 μm to 600 μm; and/or
   an Average Cell Wall Thickness of from 10 μm to 80 μm; and/or
   a thickness of from 0.5 mm to 4 mm; and/or
   a basis weight of from 50 grams/m$^2$ to 250 grams/m$^2$; and/or
   a density of from 0.05 grams/cm$^3$ to 0.5 grams/cm$^3$; and/or
   a Specific Surface Area of from 0.03 m$^2$/g to 0.25 m$^2$/g.

12. The dissolvable solid article according to claim 1, said article comprising from 4 to 50 of said flexible, dissolvable, porous sheets.

13. The dissolvable solid article according to claim 1, wherein the sheet comprises from about 30% to about 65%, by weight of the sheet, of the surfactant.

14. The dissolvable solid article according to claim 13, wherein the surfactant comprises an alkyl ether sulfate.

* * * * *